US009404900B2

(12) United States Patent
Herman et al.

(10) Patent No.: US 9,404,900 B2
(45) Date of Patent: Aug. 2, 2016

(54) SYSTEM FOR ANALYSIS OF PHASE-I AND PHASE-II METABOLITES AND PARENT COMPOUNDS WITHOUT HYDROLYSIS

(71) Applicants: Joseph Herman, West Chester, PA (US); Sarah J. Fair, Manchaug, MA (US); Dayana Argoti, Charlestown, MA (US)

(72) Inventors: Joseph Herman, West Chester, PA (US); Sarah J. Fair, Manchaug, MA (US); Dayana Argoti, Charlestown, MA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 13/724,316

(22) Filed: Dec. 21, 2012

(65) Prior Publication Data

US 2014/0178979 A1    Jun. 26, 2014

(51) Int. Cl.
*G01N 30/02*    (2006.01)
*G01N 30/08*    (2006.01)
*G01N 30/14*    (2006.01)
*G01N 30/46*    (2006.01)

(52) U.S. Cl.
CPC ............... *G01N 30/02* (2013.01); *G01N 30/08* (2013.01); *G01N 30/14* (2013.01); *G01N 30/462* (2013.01); *G01N 30/468* (2013.01); *G01N 2030/143* (2013.01)

(58) Field of Classification Search
CPC ................................. G01N 30/02; B01D 15/18
USPC ........................... 436/161; 422/63; 435/288.6
See application file for complete search history.

(56) References Cited

U.S. PATENT DOCUMENTS

| 5,117,109 A | * | 5/1992 | Asakawa et al. ............... 250/288 |
| 7,846,335 B2 | * | 12/2010 | Bisschops et al. ............ 210/656 |
| 8,123,949 B2 | | 2/2012 | Gilar et al. |
| 2006/0207941 A1 | * | 9/2006 | Morikawa ...................... 210/656 |
| 2009/0090856 A1 | * | 4/2009 | Grant et al. .................... 250/282 |
| 2010/0024527 A1 | | 2/2010 | LaMarr et al. |

FOREIGN PATENT DOCUMENTS

| EP | 1 748 293 A2 | 1/2007 | |
| GB | 1263481 A | * 2/1972 | ............. B01D 15/08 |
| WO | WO 2012/058632 A1 | 5/2012 | |

OTHER PUBLICATIONS

Beckman Instruments, Inc. (GB 1263481 A) Abstract from EAST FRPS.*

(Continued)

*Primary Examiner* — Lyle Alexander
*Assistant Examiner* — Emily Berkeley
(74) *Attorney, Agent, or Firm* — Thomas F. Cooney

(57) ABSTRACT

An apparatus comprises: a first chromatographic column fluidically coupled to a source of sample and a source of a first chromatographic mobile phase solvent; a second chromatographic column fluidically coupled to the first column; a source of a second mobile phase solvent fluidically coupled between the first and second columns; and a detector, the first chromatographic column being configurable to receive, in a trapping step, the first solvent and sample and to retain a first portion of a plurality of analytes therein and to pass a second portion of the plurality of analytes therethrough, the second chromatographic column being configurable, in the trapping step, to receive the second portion of the plurality of analytes and the first and second solvents and to retain the second portion of the plurality of analytes therein, the detector being arranged to receive the second and first portions in respective first and second elution steps.

10 Claims, 17 Drawing Sheets

(56) References Cited

OTHER PUBLICATIONS

Beckman Instruments, Inc. (GB 1263481 A) Abstract downloaded on Feb. 20, 2014 from EAST FRPS.*

Gustavsson et al., "Validation of Direct Injection Electrospray LC-MS/MS for Confirmation of Opiates in Urine Drug Testing," J. Mass Spectrom. 2007, 42, pp. 881-889.

Pizzolato et al., "LC-based Analysis of Drugs of Abuse and Their Metabolites in Urine," Trends in Analytical Chemistry, vol. 26, No. 6, 2007.

Wang et al., "Incomplete Recovery of Prescription Opioids in Urine using Enzymatic Hydrolysis of Glucuronide Metabolites," Journal of Analytical Toxicology, vol. 30, 2006.

Kawaguchi et al., "New analyser for the determination of urinary vanillylmandelic acid, homovanillic acid and creatine," Biomedical Applications, vol. 567 ( No. 1), pp. 11-19.

Du et al., "High turbulence liquid chromatography online extraction and tandem mass spectrometry for the simultaneous deterinination of suberoylanilide hydroxamic acid and its two metabolites in human serum." Rapid Commun. Mass Spectrom. 2005, 19, pp. 1779-1787.

* cited by examiner

SYSTEM FOR ANALYSIS OF PHASE-I AND PHASE-II METABOLITES AND PARENT COMPOUNDS WITHOUT HYDROLYSIS

FIELD OF THE INVENTION

The present invention relates generally to the field of sample analysis by chromatography and, more particularly, to quantitative analysis of drug compound concentrations in biological specimens.

BACKGROUND OF THE INVENTION

Liquid chromatography mass spectrometry ("LCMS") is a powerful analyte detection and measurement technique that has become the preferred method of detecting small molecule, amino acid, protein, peptide, nucleic acid, lipid, and carbohydrate analytes to a high accuracy for diagnostic purposes. The chromatographic separation process relies on the fact that a number of component solute molecules in a flowing stream of a fluid percolated through a packed bed of particles, known as the stationary phase, can be efficiently separated from one another. Generally, separation in liquid chromatography is achieved in a column by selective distribution of the sample molecules between a stationary phase and a mobile phase. The individual sample components are separated because each component has a different affinity for the stationary phase, leading to a different rate of migration for each component and as different exit time for each component emerging from the column. The separation efficiency is determined by the amount of spreading of the solute band as it traverses the bed or column.

Reversed-phase liquid chromatography (RPLC) is widely used as a mode of separation in chromatographic systems. In the RPLC technique, the solvent(s) employed in the mobile phase is/are more polar than the stationary phase, whereas the reverse situation is true in conventional (normal phase) chromatography. The mobile phase solvents typically employed in reversed phase liquid chromatography systems comprise water and one or more water-miscible organic modifiers, for example, acetonitrile or methanol. Analyte species of-interest typically form a solution with the mobile phase. The RP-HPLC stationary phase is usually highly hydrophobic or non-polar. The affinity of a chemical species for a stationary phase, which affects the rate at which the particular species in a flowing mobile phase passes through the stationary phase, results primarily from interaction of the species with chemical groups present on the stationary phase. These chemical groups may be provided on the stationary phase by reacting a surface-modifying reagent with a substrate, such as a silica substrate. Surface-modifying agents may thus be employed to adsorb specific chemical groups onto the stationary phase. Conventional reversed-phase liquid chromatography uses 1.5-10 µm spherical silica beads that have been modified by covalent attachment of hydrocarbon chains including 4, 8, or 18 carbon atoms to provide a non-polar surface.

Clinical laboratories routinely measure the concentrations of drug compounds (including pharmaceutical compounds as well as other natural and synthetic drugs of abuse) in human-provided body fluids. These COM pounds generally cart low molecular weight molecules that are very hydrophilic and difficult to retain on most reversed phase LC systems. The metabolites are even more hydrophilic and are even harder to retain on reverse phase LC systems. Alternative HPLC systems, such as those employing HILIC columns, retain the metabolites but not all of the parent compounds. Thus, quantification of drug compounds using chromatographic separation techniques is quite challenging. For this reason, current clinical quantification of drugs of abuse is carried out by hydrolysis of the phase two metabolites and some phase one metabolites (either by acid or enzymatic hydrolysis) in order to convert the metabolite back to the parent compound and subsequently, LCMS measurement of only the parent compound is necessary. The total concentration of the metabolites and parent drug are reported together as a single value because the metabolites have been converted back to the parent during hydrolysis. Either acid hydrolysis or enzymatic hydrolysis requires a treatment step followed by up to 2 hours of incubation at an elevated temperature. Thus, the hydrolysis procedure adds extra time and cost to each analysis.

In accordance with the above discussion, there is a need in the art for a quick and reliable chromatographic separation and analysis methods—such as an LCMS method that does not require an additional hydrolysis step—for routine clinical measurements of drug compounds. There is also a need for new chromatographic designs that are able to implement the new methods. Unfortunately, the conventional instrumentation required for LCMS is technically complex and not well suited to the typical hospital clinical lab or medical lab technician. These clinical labs have not adopted LCMS diagnostics and, instead, generally use alternative diagnostic techniques, including automated immunoassay. Alternatively, the clinical labs may send the samples out to a central reference laboratory for analysis.

Recently, however, an automated analyzer that is suitable for routine clinical and hospital use has recently been described in international patent application (PCT) publication WO 2012/058632 A1 titled "Automated System for Sample Preparation and Analysis" which is hereby incorporated by reference herein in its entirety. Adaptation of such an automated analyzer so as to further include routine analyses for drugs of abuse using one of the conventional hydrolysis methods would require either off-line hydrolysis followed by transfer of the treated samples to the automated analyzer or else on-board automated robotic hydrolysis. Implementation of either of these modifications would require additional hardware and increased overall system complexity. Further, a recent study (Wang et al., "Incomplete Recovery of Prescription Opioids in Urine using Enzymatic Hydrolysis of Glucuronide Metabolites", Journal of Analytical Toxicology, Vol, 30, Oct. 2006, pp. 570-575) has concluded that, with regard to at least opioids in urine samples, acid hydrolysis liberates a greater proportion of the parent drug compounds and introduces less variability than enzymatic hydrolysis. To implement the evidently preferred method of acid hydrolysis for such samples would require additional expensive safeguards to prevent lab personnel from being exposed to hazardous reagents. Therefore, there is a special need in the art for a quick and reliable chromatographic separation and analysis method—such as an LCMS method that does not require an additional hydrolysis step—that may be employed using an automated clinical analyzer to make routine clinical measurements of drug compounds,

SUMMARY OF THE INVENTION

In order to address the above-noted needs in the art, the inventors provide methods and apparatus which permit removal of hydrolysis steps for quantifying drug compounds in biological samples. Methods in accordance with the present teachings include measuring metabolites and parent compounds using two columns in a single LCMS run and then reporting the sum of the all the related compounds so as to calculate concentrations of the original parent compounds and derive the same values as would be generated by performing traditional hydrolysis.

Accordingly, in a first aspect of the invention, a liquid chromatography apparatus for detecting and quantifying a plurality of analytes in a sample is provided, wherein the apparatus comprises: a first chromatographic column fluidically coupled to a source of the sample and to a source of a first chromatographic mobile phase solvent; a second chromatographic column fluidically coupled to the first chromatographic column; a source of a second mobile phase solvent fluidically coupled between the first and second chromatographic columns; and a detector fluidically coupled to the second chromatographic column, wherein the first chromatographic column is configurable to receive, in an analyte trapping step, the first mobile phase solvent and the sample and to retain a first portion of the plurality of analytes therein and to pass a second portion of the plurality of analytes therethrough, wherein the second chromatographic column is configurable, in the analyte trapping step, to receive the second portion of the plurality of analytes and the first and second mobile phase solvents and to retain the second portion of the plurality of analytes therein, and wherein the detector is arranged to receive the second and first portions of the plurality of analytes in a first and in a second elution step, respectively.

In a second aspect of the invention, a method for analyzing and quantifying a panel of drugs in a clinical sample is provided, wherein the method comprises: trapping a first portion of drug parent compounds and their metabolites on a first chromatographic column; trapping a second portion of the drug parent compounds and their metabolites on a second chromatographic column; separately eluting the first and second portions of the drug parent compounds and their metabolites from the first and second chromatographic columns; detecting concentrations of each of the drug parent compounds and metabolites eluted from each of the first and second chromatographic columns with a detector; and summing the detected concentration of each drug parent compound together with the detected concentrations of all of its respective analytes so as to derive, a respective total concentration of each drug in the sample.

In another aspect of the invention, there is provided an automated sample preparation and analysis system comprising: (a) an automated sample preparation station for preparing a plurality of samples in accordance with a plurality of assays that are selected from a database containing a plurality of unique assays; (b) a sample analysis station for automatically performing the plurality of assays; and (c) a transport mechanism for transporting prepared samples from the sample preparation station to the sample analysis station, wherein the sample analysis station comprises: (i) a source of a first chromatographic mobile phase solvent; (ii) a source of a second chromatographic mobile phase solvent; (iii) a first chromatographic column fluidically coupled to the first chromatographic mobile phase solvent and configured to receive a portion of the prepared samples from the sample transport mechanism, (iv) a second chromatographic column fluidically coupled to the first chromatographic column and to the source of the second chromatographic mobile phase solvent; and (v) a detector fluidically coupled to the second chromatographic column, wherein the first chromatographic column and the second chromatographic column are operable to trap, respectively, a first portion and a second portion of a panel of drug compounds and their metabolites during a trapping step and to elute, respectively, the first and second portions of the drug compounds and their metabolites to the detector.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

Figure 1A:
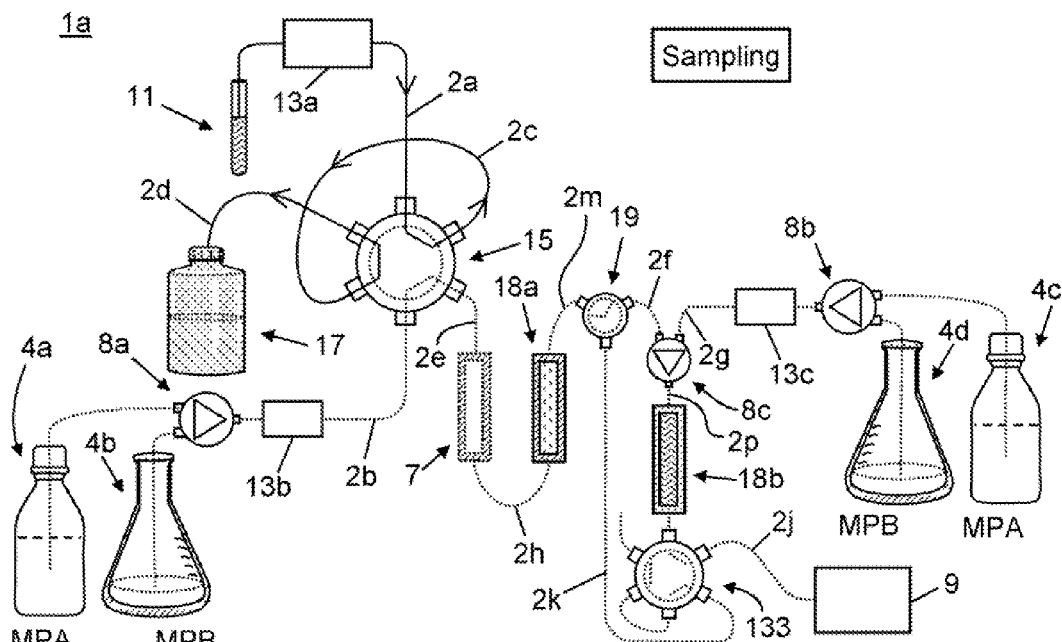
FIGS. 1A-1D are diagrams of a first chromatographic system in accordance with the present teachings, illustrating sampling and analyte trapping and elution steps.

The present invention provides methods and apparatus for analyzing drug compounds in biological samples and is provided in the context of a particular patent application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-12 taken in conjunction with the following discussion.

FIGS. 1A-1D depict a chromatographic system, shown generally at 1a, and a method for employing the system in accordance with one aspect of the present teachings. The sample will generally comprise a mixture of biologically-derived fluid in a solvent. For purposes of this discussion, it is assumed that the sample includes at least two analyte compounds—a first analyte compound comprising a drug molecule and at least one other compound comprising a metabolite (such as phase-I or a phase-II metabolite) of the drug molecule. The sample may include additional analyte compounds such as additional metabolites of the drug molecule as well as possibly additional drug molecules and their respective phase-I and phase-II metabolites.

As illustrated in FIGS. 1A-1D, the exemplary chromatographic system 1a comprises a multiport valve 15, such as a 6-port valve of a type commonly used in chromatographic systems. Such 6-port valves may be employed in either one of two different configurations: a first configuration in which the first, third and fifth ports are respectively fluidically coupled to the second, fourth and sixth ports and a second configuration in which the first, third and fifth ports are respectively fluidically coupled to the sixth, second and fourth ports. As shown, a first port of the valve 15 is fluidically coupled to a sample contained in a sample source 11 by means of fluid tubing line 2a. The sample may be delivered to the valve 15 under the impetus of a first fluid pump 13a. Another port of the valve (in this example, the fourth port) is fluidically coupled to at least two sources of mobile-phase solvents which, in this example, are the two solvents denoted as "Mobile Phase A" (MPA) in solvent source 4a and "Mobile, Phase B" (MPB) in solvent source 4b. The solvents may be delivered to the valve port separately or in any mixed proportion through fluid tubing line 2b, the exact proportions being controlled by a first gradient valve 8a.

Two ports of the multiport valve 15 are fluidically coupled, respectively, to the two ends of a looped fluid tubing line 2c which may be used for temporary storage of a portion of the sample prior to its being mixed with one or more of the mobile phase solvents. Another port of the multiport valve 15 is fluidically coupled to a waste container 17 by means of fluid tubing line 2d and a final port of the valve (in this example, the third port) is fluidically coupled to outlet fluid tubing line 2e. It should be noted that the terms "fluid tubing", "fluid tubing line", "fluid tubing segment" and similar terms as used herein are not intended to necessarily limit the embodiments to the use of tubing portions, in a strict sense, but are meant to include other alternative forms of fluid transfer lines or passageways such as, for example, channels or grooves in plates or bores in solid components.

The outlet fluid tubing line 2e of the system 1a (FIGS. 1A-1D) delivers a sample portion (previously stored in looped fluid tubing line 2c) together with mobile phase solvent or solvents to the chromatic separation columns (analytical columns) 18a and 18b. An additional preparatory or "cleanup" column 7—such as a solid-phase extraction (SPE) or a Turboflow™ column—may optionally be included upstream from the analytical columns 18a and 18b in order to remove interfering or unwanted compounds from the sample mixture prior to delivery of the sample to the two analytical columns. For example, the preparatory column 7 may be employed in order to remove certain classes of non-analyte compounds from the sample. If a preparatory column is used, than an additional fluid tubing segment 2h may be included between the preparatory column 7 and the first analytical column 18a, The optional preparatory or "cleanup" column 7 is shown in phantom in FIG. 1 and others of the drawings to indicate that, in many experimental situations, it may not be required. For instance, many drug samples are analyzed in a urine matrix—in such cases, the column 7 is generally unnecessary. If such assays are performed on plasma or whole blood samples, however, then the column 7 may be required.

The properties of the first analytical column 18a are chosen such that, when the sample mixed with a particular mobile phase composition—as determined by the particular MPA and MPB compositions and by the amount of mixing (if any) between them as controlled by gradient valve 18a—is caused to pass through the first analytical column, then only compounds whose hydrophobicity is greater than a certain level or lesser than a certain level are retained within this column. Practically, this condition means that the majority of drug-related analytes that are retained in this column will be either one or the other of the drug parent compounds or the metabolites. Under these conditions, the non-retained analytes pass completely through the first analytical column to the second analytical column 18b (see FIG. 1B) by means of fluid tubing line 2m, selection valve 19, fluid tubing line 2f, gradient valve 8c and fluid tubing line 2p. In some embodiments, the gradient valve 8c may be replaced by a simple tee-junction. Thus, component 8c may be taken to represent a gradient valve or, alternatively, a tee-junction. It should be noted that, in the various figures, solid lines are used to denote fluid tubing segments through which fluids flow during, a particular step or operation whereas dotted lines are used to denote fluid tubing segments (or other fluid transfer lines) where fluid flow is not necessary for the performing of the step or operation. (Note, however, that fluid may nonetheless flow through the dotted-line fluid tubing lines in conjunction with other operations possibly occurring in parallel with the indicated step or operation.) Dash-dot lines indicate fluid flow which may be optionally drawn from a first source, from a second source or simultaneously from both sources. The solid-line dash-dot representations of various fluid tubing lines are overlain by arrows to indicate the directions of flow in the various diagrams.

The gradient valve or tee-junction 8c permits delivery of a different or additional mobile phase composition to the second analytical column 18b. In the illustrated example, the different or additional mobile phase composition may comprise one of or a mixture of the compositions MPA and MPB provided in solvent sources 4c and 4d, respectively, Alternatively, the mobile phase compositions provided in solvent sources 4c and 4d could be different from those provided in solvent sources 4a and 4b. A gradient valve 8b may be provided in order to choose between and/or mix the mobile phase compositions provided in solvent sources 4c and 4d and a fluid pump 13c is provided to deliver the different or additional mobile phase composition to gradient valve (or tee junction) 8c via fluid tubing segment 2g.

Analyte compounds that elute from either the first analytical column 18a or the second analytical column 18b are detected by a detector 9, which may comprise a mass spectrometer. The selection valve 19 enables the flow of analyte compounds that elute from the first analytical column 18a to bypass the second analytical column 18b as these eluting analyte compounds are transferred to the detector. Accordingly, the bypass valve 19 is selectable between at least two different fluid routing configurations, as illustrated by comparison between FIG. 1B and FIG. 1D. In a first configuration (e.g., FIG. 1B) the bypass valve 19 enables a flow of sample to pass through both analytical columns 18a, 18b in sequence so that a first set of analytes may be retained on the first analytical column 18a and a second set of analytes from the same sample may be retained on the second analytical column 18b. However, in a second configuration, (e.g., FIG. 1D) the bypass valve 19 causes a flow of analytes eluting from the first analytical column 18a to be diverted to fluid tubing line 2k, thereby bypassing the second analytical column 18b. The outputs from each of the two analytical columns are directed to the detector 9 through multiport valve 133 and fluid tubing line 2j.

As noted above, under operation of the chromatographic system 1a, only those drug analytes (a majority of which will be either the drug parent compounds or the drug metabolites) that are not retained in the first analytical column 18a are passed through to the second analytical column 18b. Accordingly, the properties of the second analytical column 18b are chosen such that, during the trapping step (FIG. 1B), those analytes that are passed to this second analytical column are retained on it under the flow of a mobile phase composition provided either through fluid tubing line 2f, fluid tubing line 2g or as a mixture of the mobile phase compositions provided through both fluid tubing lines 2f and 2g. Operation of the chromatographic system 1a necessarily includes elution steps (FIGS. 1C, 1D) in addition to analyte trapping steps. The mobile phase composition employed during elution of analytes from a column may be different from that employed during trapping of the analytes onto the column.

Figure 10:
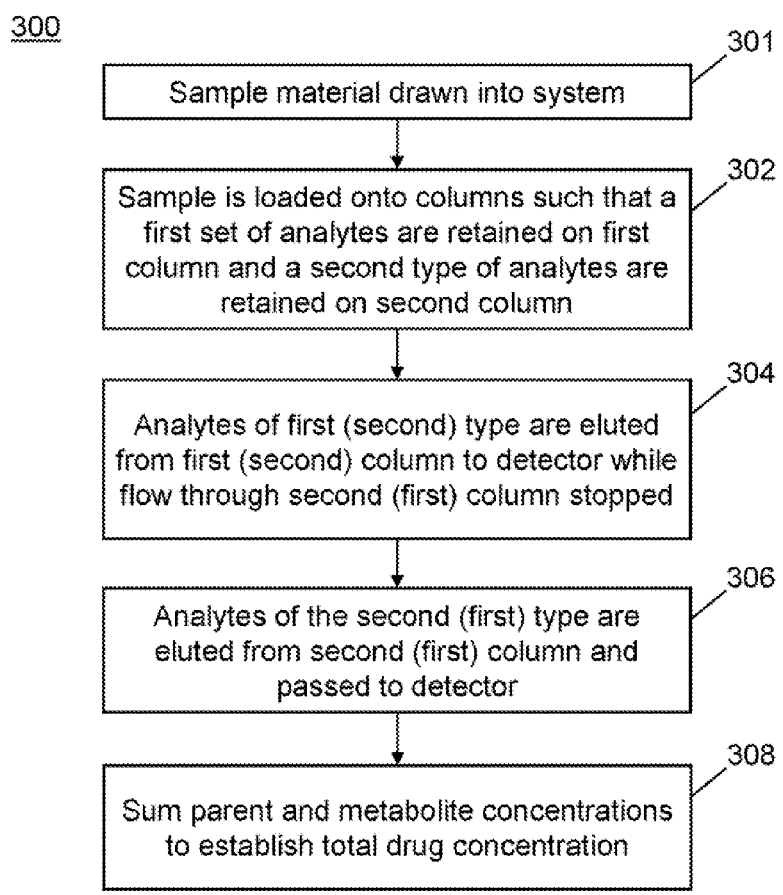
FIG. 10 is a flowchart, of a general method for operating a chromatographic system in accordance with the present teachings.

The basic steps in a general method for operating the system 1a are provided in method 300 illustrated in FIG. 10. In the first step. Step 301, sample material is transferred into the chromatographic system from an external container. In Step 302, at least a portion of the sample is loaded onto the analytical columns 18a, 18b such that analytes belonging to a first type or category (e.g., either parent drug compounds or drug metabolite compounds) or having a first state or condition (e.g., a condition of being either above or below a threshold or level) of a particular property or characteristic (e.g., the property of hydrophobicity) are retained on a first one of the columns (18a and 18b) and such that analytes belonging to a second type or category or having a different state or condition of the particular property or characteristic are retained the other one (a second one) of the two columns. This step may take advantage of differences in the degree of hydrophobicity between the two types or categories of analytes.

In general, any particular analyte will have a ratio of concentration distribution between two immiscible solvents (e.g., an aqueous solvent and an organic-rich solvent) at equilibrium, which is referred to as the partition coefficient. Said another way, the partition coefficient is a measure of a desired analyte's hydrophilicity ("water loving") or hydrophobicity ("water fearing"). Often the partition coefficient is reported as the logarithm of the partition coefficient, referred simply as "logP." It would be readily appreciated that because logP is logarithmic in nature, each unit represents a difference in hydrophobicity by factor of 10. Thus, two analytes having similar logP values may have similar hydrophobicities (i.e., chemistry) and may be easily separated by the same mobile and stationary phases two analytes having different logP values tend to result in vastly different retention characteristics on the same LC system and may require quite different mobile and/or stationary phases to achieve a desired chromatographic separation. As a consequence, analytes are conventionally grouped together according to similar logP values and run in batch modes using the same mobile phase and mass spectrometer settings.

Although both drug parent compounds and their metabolites are considered to be hydrophilic, the metabolites are generally even more hydrophilic (that is, less hydrophobic) than the parent compounds. In Step 304, analytes of either the first or the second type or category are eluted from the first or second one of the two columns, respectively, thereby causing separation of the various analytes of the first (second) type or category according to their respective retention times. During this step, the thus-separated analytes are passed to a detector (such as a mass spectrometer) for quantification while flow through the other one of the columns is stopped. Subsequently, in Step 306, analytes of the other type or category are eluted from the other one of the two columns, thereby causing separation of the various analytes eluting from that other column according to their respective retention times. These analytes eluting from the other column are also passed to the detector. In some system embodiments (e.g. the system 3 illustrated in FIG. 3), the system may comprise a physical configuration in which these second-eluting analytes pass through a different analytical column (without being retained in that different column) as they are transferred to the detector for quantification during this step. In such embodiments (e.g., FIG. 3), these second-eluting analytes are not retained within the different analytical column during this step because, during this step, the column stationary phase and the mobile phase are chosen such that these analytes have a strongly preferential affinity for the mobile phase. Finally, in Step 308, the total concentration of any particular drug in the sample is calculated by summation of the quantified parent compound together with the quantified concentrations of all of its metabolites.

FIGS. 1A-1D graphically depict the various steps during implementation of one exemplary embodiment of the method 300. For purposes of this particular example only, it is assumed that only the parent compounds (e.g., residual unmetabolized drugs) are retained on the column 18a and that only the metabolite compounds are retained on the column 18b. The column 18a may comprise an Accucore™ C18 column commercially available from Thermo Fisher Scientific of Waltham Mass. USA and the column 18b may comprise a Synergi™ Polar RP column commercially available from Phenomenex, Inc. of Torrance, Calif. USA. Specifically, the stationary phases of Accucore™ columns use particles having 2.6 μm solid-core material and having a very tight particle size distribution. The particles can be described as a solid silica core surrounded by a porous outer layer. The very tight particle size distribution of this material results in columns with high permeability, and, therefore, for the same nominal pressure, better chromatographic separations are achieved than those utilizing fully porous materials. The solid-core and the well defined porous outer layer provides shorter diffusion paths into the stationary phase compared with those in fully porous particles, thus reducing band broadening and improving separation efficiency. The surface treatment of the substrate of the stationary phase of the Synergi™ Polar RP column comprises a polar endcapped ether-linked phenyl phase that provides polar and aromatic reversed phase selectivity. Using these columns, suitable choices of "Mobile Phase A" (MPA) and "Mobile Phase B" are, respectively, a solution of 10 millimolar (10 $mol/m^3$) ammonium formate and 0.05% formic acid in water and a solution of 10 millimolar (10 $mol/m^3$) ammonium formate and 0.05% formic acid in methanol.

As shown in FIG. 1A, an analyte-bearing sample is, in a first step, provided from sample source 11 through fluid tubing, line 2a. The sample is delivered to a port of the multi-port valve 15 through tubing 2a under the impetus of pump 13a. The multi-port valve 15 is configured, during this step, to deliver the mixture containing the sample portion to be analyzed to looped tubing 2c. Any excess solvent or sample is delivered to waste container 17 through tubing 2d, which is fluidically coupled to another port of the multi-port valve.

Figure 1B:
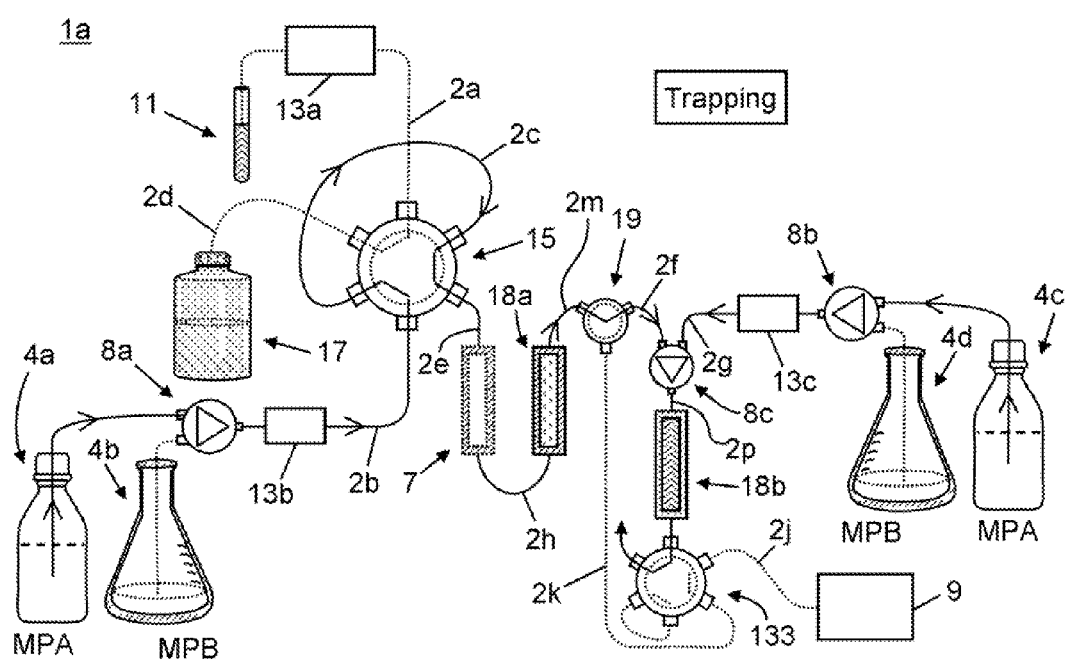

After collection of a portion of the mixture containing the sample portion to be analyzed, the valve 15 is reconfigured as shown in FIG. 1B so as to expel the sample material from the tubing 2c and to transfer the sample, through fluid tubing lines 2e and 2m, selection valve 19, fluid tubing line 2f and gradient valve or tee-junction 8c to the pair of analytical chromatographic columns 18a and 18b. The sample may also pass through an optional cleanup or preparatory column 7 as well as fluid tubing line 2h prior to entering the first analytical column, in this "trapping" configuration, the aqueous mobile phase solvent (MPA) provided by solvent source 4a (possibly mixed with some proportion of solvent MPB from solvent source 4b) is caused to flow, under the impetus of pump 13b, through gradient valve 8a and tubing 2b so as to enter a port of the multi-port valve 15 and thereby mix with and expel the mixture portion previously collected in tubing 2c. The expelled mixture of sample and solvents passes through tubing segment 2e (and, optionally, column 7 and tubing segment 2h) to the chromatographic column 18a.

During the trapping stage or step (FIG. 1B), the mobile phase solvent is chosen such that the analyte or analytes comprising drug parent compounds are preferentially partitioned onto the stationary phase of column 18a. The mobile phase and the remaining analyte or analytes—comprising one or more drug metabolites—pass through column 18a without being retained thereon. The analyte or analytes of this second category of analytes pass through the selection valve 19 and a fluid tubing segment 2f to the gradient valve or tee-junction 8c. At this point, a second aqueous mobile phase MPA delivered from solvent source 4c may be passed through gradient valve 8b and tubing segment 2g under the impetus of fluid pump 13c so as to be mixed into the sample and first mobile phase mixture at the gradient valve, or tee-junction 8c. This mixing of a different mobile phase composition phase into the sample material may increase the preferential partitioning of the hydrophilic drug metabolite compounds onto the stationary phase of the column 18b for retention thereon. During this trapping step, any fluids previously residing in the chromatographic columns, fluid tubing lines or other system components exit the second column and pass to the valve 133 which, in this step, is configured so as to transfer such previously resident fluids to a waste container 17.

Figure 1C:
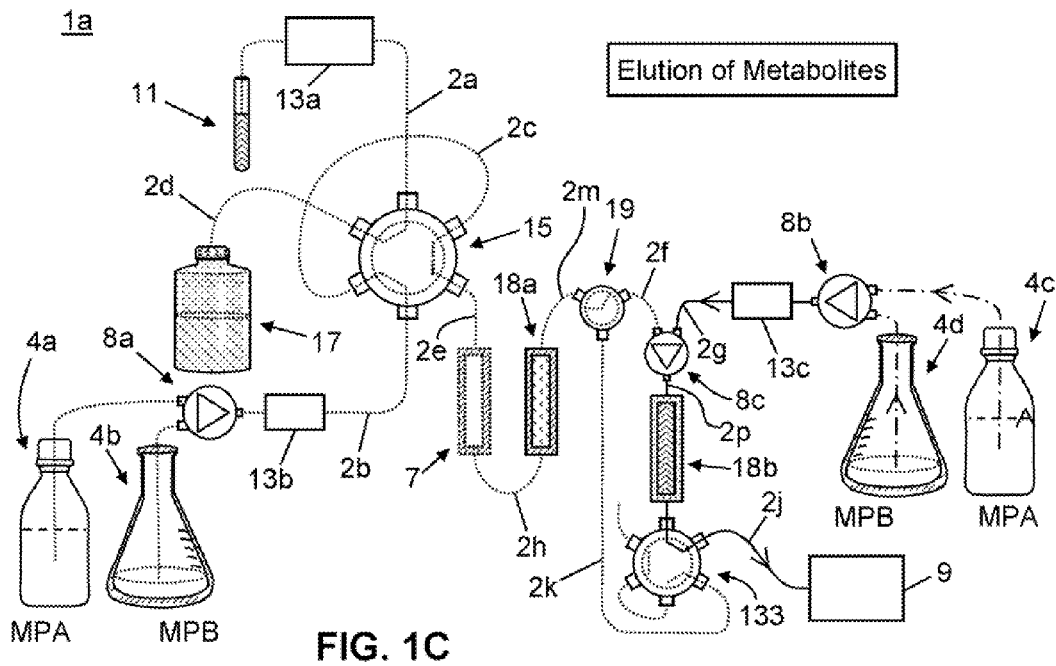

FIG. 1C illustrates elution of the drug metabolite compounds from the column 18b, such as is outlined in Step 304 of method 300 (FIG. 10). In this step, the flow of mobile phase solvents from solvent sources 4a and 4b is stopped (possibly by stopping the pump 13b or adjusting the configuration of either the selection valve 19 or the gradient valve 8c) so as to only pass flow provided from tubing segment 2g. Also, during this step, the flow of mobile phase to the column 18b is switched or ramped so as to comprise at least a percentage of the organic MPB solvent provided by solvent source 4d, possibly by configuring the gradient valve 8b so that the pump 13c draws solvent exclusively from solvent source 4d or possibly simultaneously from both solvent sources 4c, 4d. The controlled relative proportions of aqueous and organic solvents in this mobile phase are chosen so as to cause partitioning of the retained metabolite compounds into the mobile phase and elution of these compounds from the column 18b so as to pass to the detector 9 through valve 133 and tubing segment 2j.

Figure 1D:
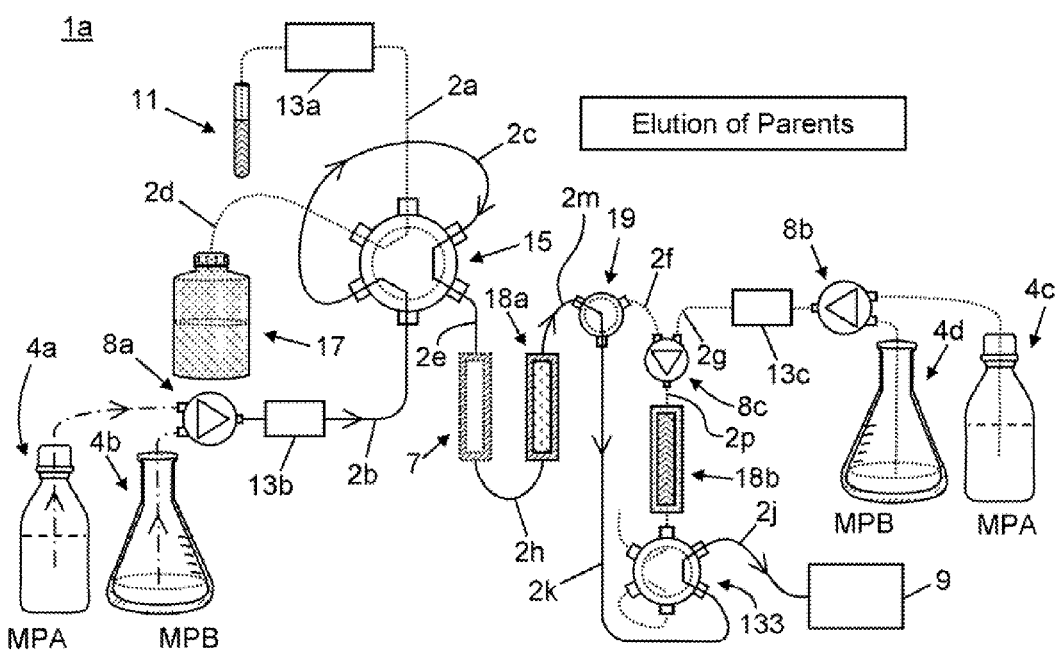

FIG. 1D illustrates subsequent elution of the drug parent compounds from the column 18a (see Step 306 of method 300 in FIG. 10, During this step, flow of mobile phases from sources 4c and 4d is stopped and the selection valve 19 is configured so as to direct the flow of analytes eluting from the first analytical column 18a to the bypass fluid tubing line 2k. The mobile phase solvent is chosen so as to comprise at least a percentage of the organic MPB solvent, possibly by configuring the gradient valve 8a so that the pump 13b draws solvent exclusively from solvent source 4b or possibly simultaneously from both solvent sources 4a, 4b. This mobile phase flows through fluid tubing line 2b, multi-port valve 15, and fluid tubing line 2e so as to ultimately enter the column 18a. The controlled relative proportions of aqueous and organic solvents in this mobile phase are chosen so as to cause partitioning of the retained parent drug compounds into the mobile phase and elution of these compounds from the column 18a. The eluted parent drug analytes are directed into fluid tubing line 2k by the selection valve 19 to multiport valve 133, which is configured to then pass the mobile phase carrying these analytes through fluid tubing segment 2j to the detector 9.

The above-described example of the operation of the chromatographic system 1a (FIGS. 1A-1D) assumes that the parent compounds (e.g., residual unmetabolized drugs) are retained on the column 18a and that the metabolite compounds are retained on the column 18b. However, the system 1a may be configured in a reverse sense, such that the parent compounds are retained on the second analytical column 18b and that the metabolite compounds are retained on the first analytical column 18a. For purposes of illustration only, it is assumed in the following example that all such parent compounds are retained on the column 18b and that all such metabolite compounds are retained on the column 18a. To operate the system in this latter fashion, the column 18a may be provided as a hydrophilic interaction liquid chromatography (HILIC) column and the column 18b may be provided as a reversed phase column such as the Accucore™ C18 column described above or another C18 column. In order to interpret the diagrams in FIGS. 1A-1D in conjunction with this choice of columns, the identities of the MPA and MPB solvents should be reversed from that described above—that is, let the MPA solvent comprise an organic solvent and let the MPA solvent comprise an aqueous solvent.

Continuing to assume that that the column 18a comprises a HILIC column, that the column 18b comprises a reversed-phase column and that the MPA provided from solvent source 4a comprises an organic-rich solvent, then, with reference to FIG. 1B, the very hydrophilic drug metabolite analytes will associate with the polar stationary phase of the HILIC column 18a and be retained on this column. At the same time, the drug parent compounds will flow to the gradient valve 8c at which point an aqueous mobile phase (MPB) provided from solvent source 4d will be mixed with these analytes. This mixing reduces the percentage organic content of the mobile phase, thus permitting the somewhat-less-hydrophilic parent drug analytes to be retained in the column 18b. After this trapping step, elution of the parent compounds (FIG. 1C) from the column 18b proceeds by stopping flow from fluid tubing line 2f and causing the organic solvent MPA provided from solvent source 4c to flow through tubing 2g to gradient valve 8c and then to the column 18b through fluid tubing line 2p. The organic solvent MPA may be mixed with the aqueous solvent MPB from solvent source 4d, at this stage. Elution of the drug metabolite analytes then proceeds (FIG. 1D) by stopping flow from fluid tubing line 2g and causing the aqueous solvent MPB provided from solvent source 4b to pass through the column 18a. The highly hydrophilic metabolite compounds will then partition into this aqueous mobile phase, causing elution. These metabolite compounds will then remain in the aqueous mobile phase as they pass through fluid tubing line 2k and multiport valve 133 and will flow on to the detector 9 for quantification.

Figure 1E:
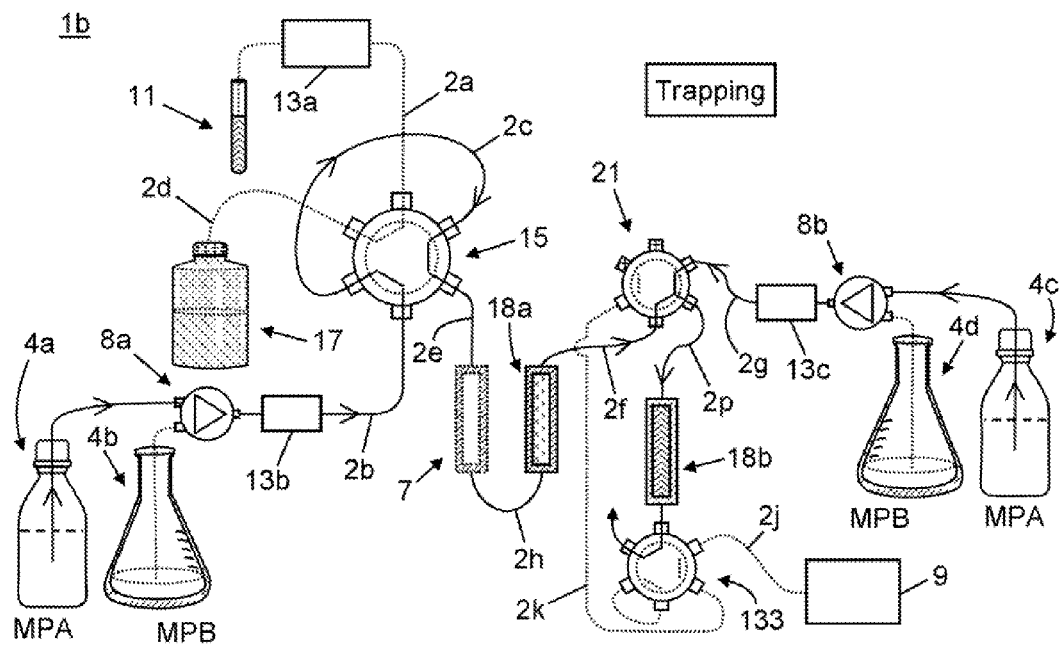
FIGS. 1E-1G are diagrams of a second chromatographic system in accordance with the present teachings, illustrating analyte trapping and elution steps.
Figure 1F:
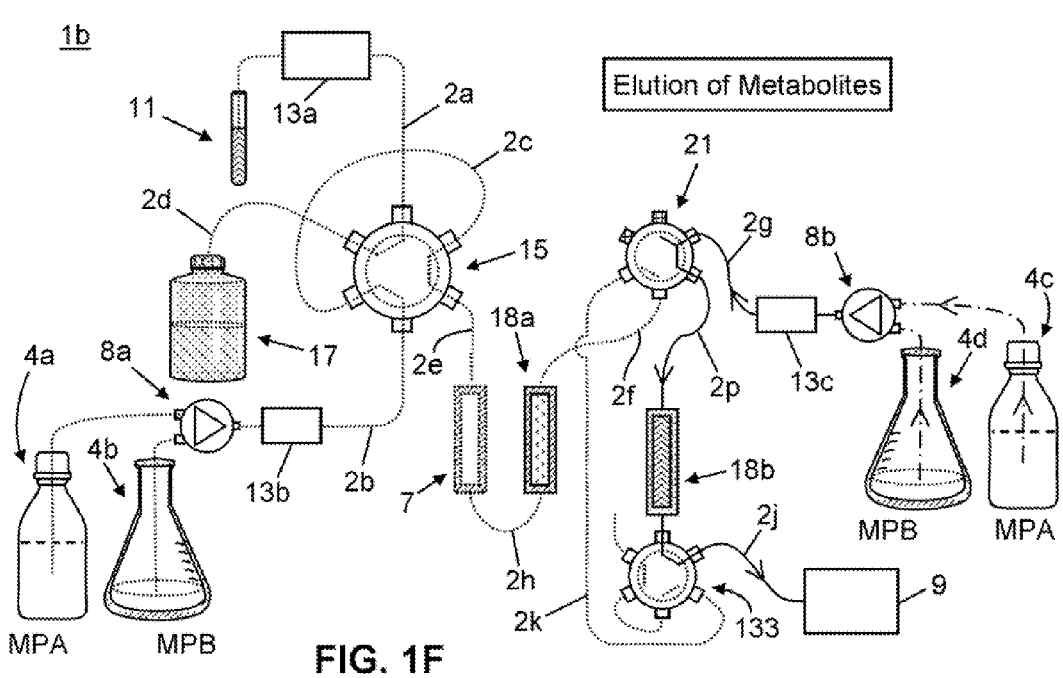
Figure 1G:
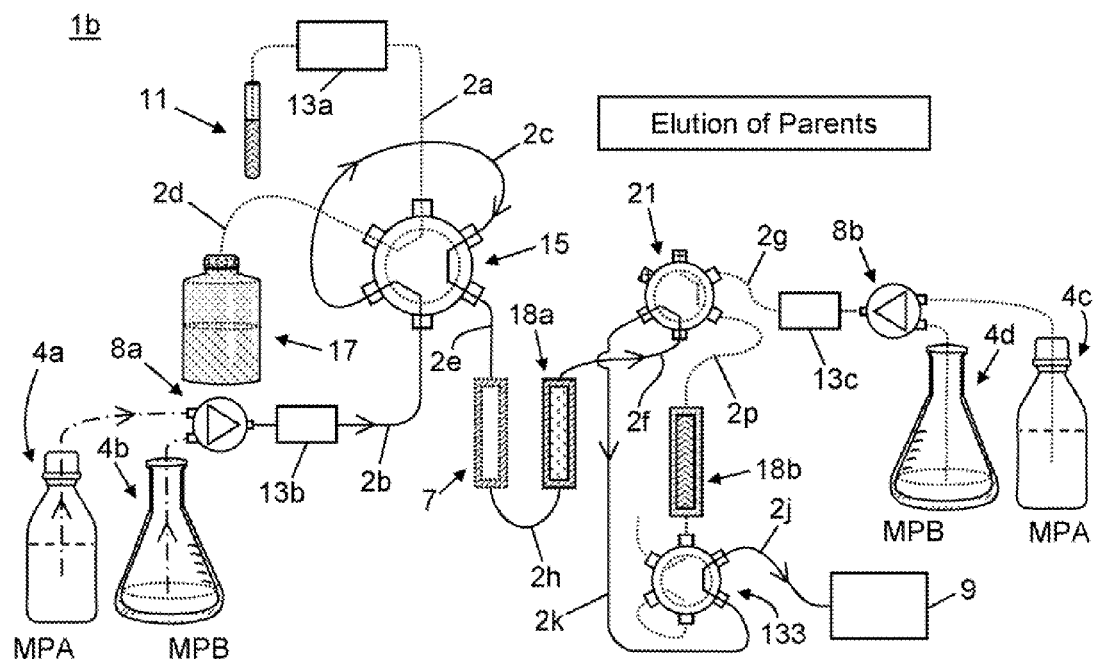
Figure 2:
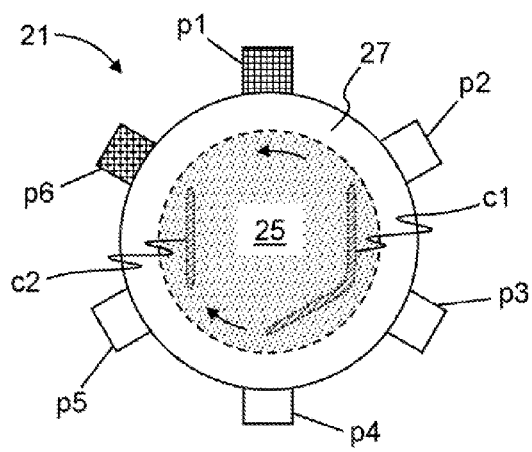
FIG. 2 is a schematic depiction of a multiport valve as may be employed in the chromatographic system depicted in FIGS. 1E-1G.
Figure 3A:
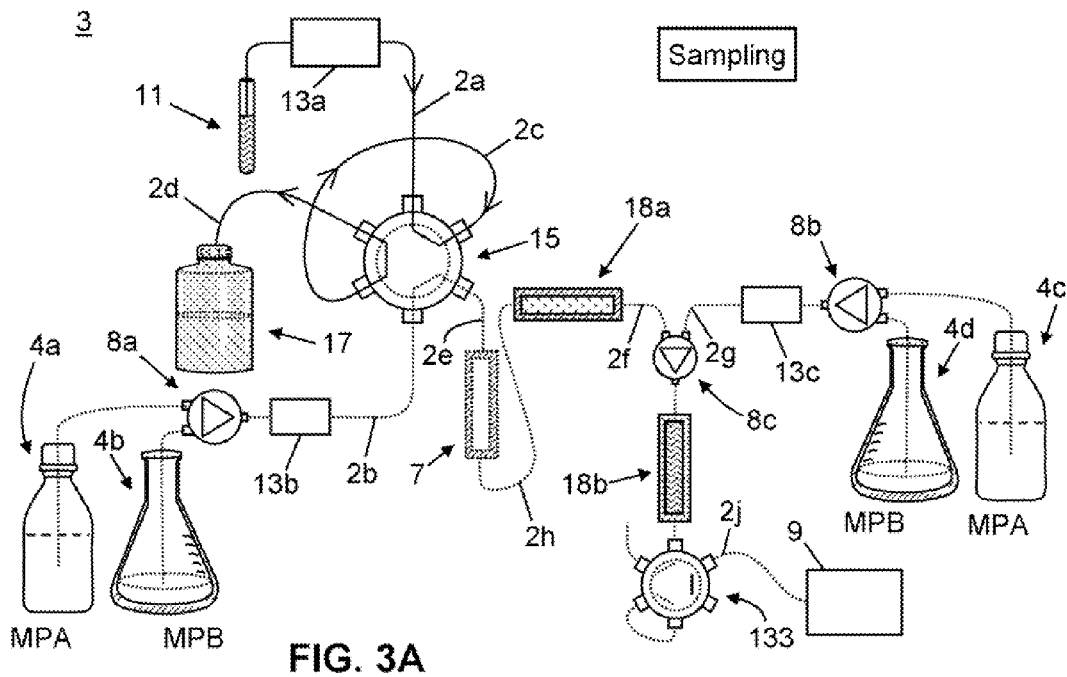
FIG. 3A-3D are diagrams of a third chromatographic system in accordance with the present teachings, illustrating sampling and analyte trapping and elution steps.
Figure 3B:
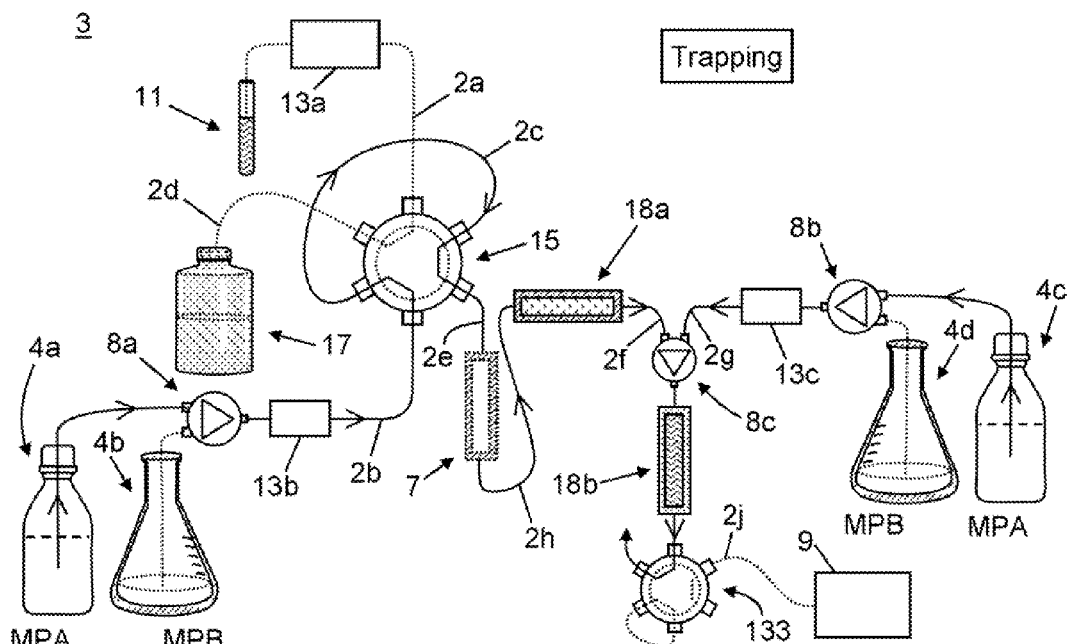
Figure 3C:
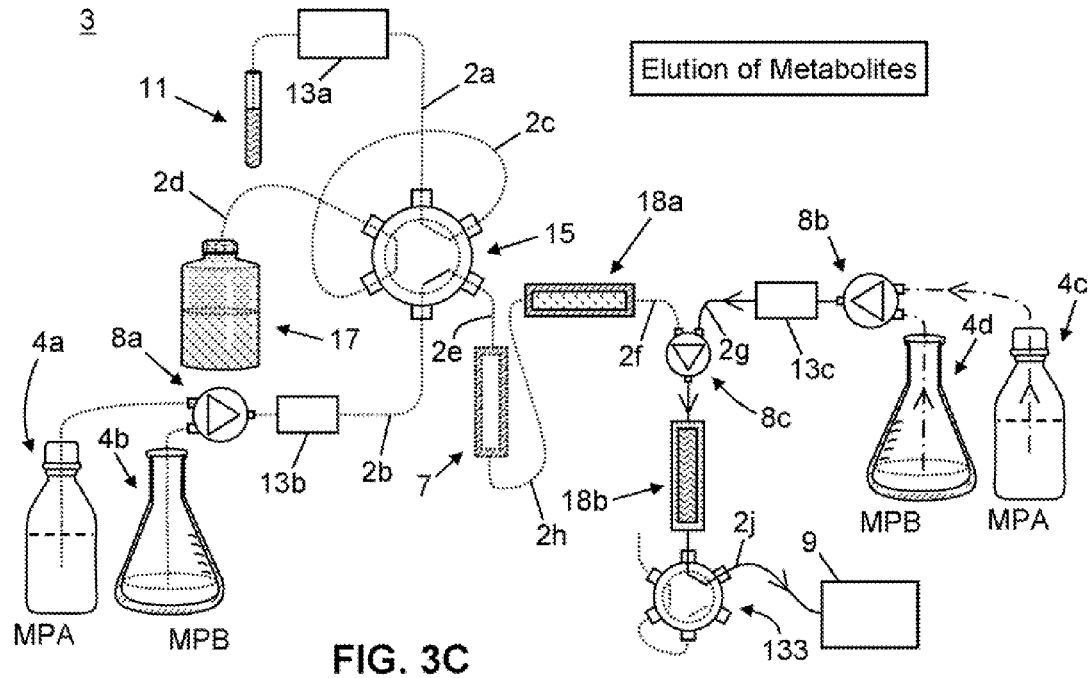
Figure 3D:
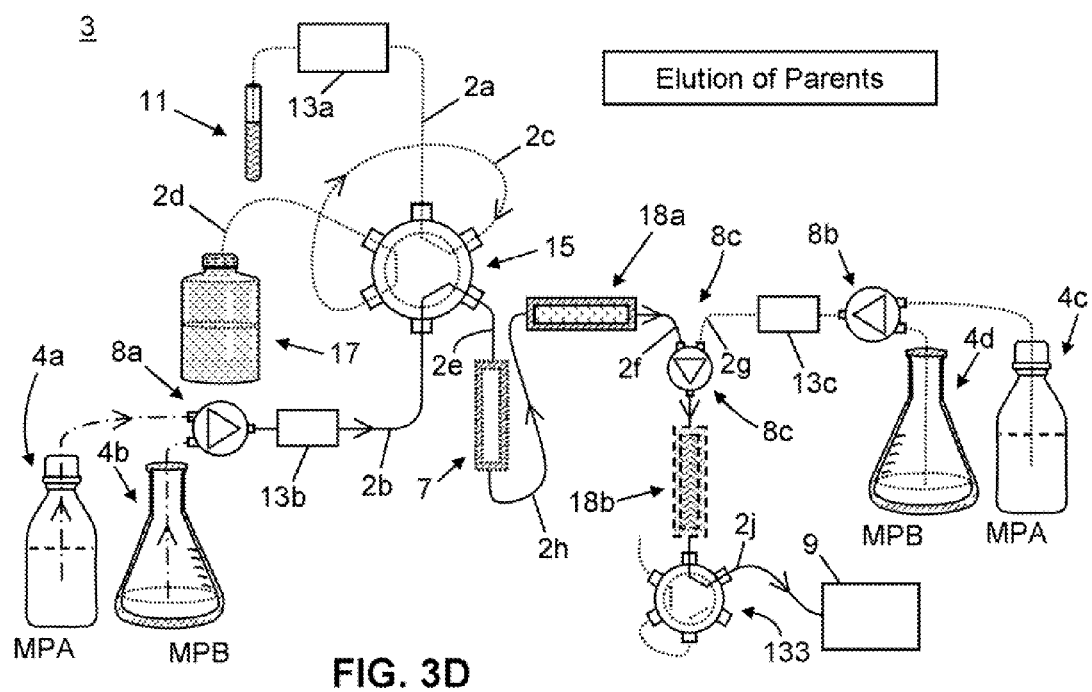

FIGS. 1E-1G are diagrams of analyte trapping and elution steps of a second chromatographic system—chromatographic system 1b—in accordance with the present teachings. The system 1b (FIGS. 1E-1G) is modified from the system 1a (FIGS. 1A-1D) by replacement of the two components comprising the selection valve 19 and the gradient valve (or tee-junction) 8c by a single multi-port valve 21. FIG. 2 is a schematic enlarged diagram of a multiport valve as may be employed in the chromatographic system 1b (FIGS. 1E-1G). As illustrated, the multiport valve 21 comprises an inner rotor member 25 which rotates on one or more bearing surfaces against an outer stator member 27. The stator member comprises several fluidic ports—in the illustrated example six ports—that are available for fluidic connection to various fluid tubing lines. In FIG. 2, these fluidic ports are designated as ports p1-p6. For use in conjunction with the chromatographic system 1b (FIGS. 1E-1G) it is desirable to have two of the ports plugged, as may be simply accomplished by means of connecting simple endcaps to these ports. Accordingly, ports p1 and p6 are illustrated with cross hatching as being plugged in FIG. 2.

The stator member of the multiport valve 21 comprises at least two internal fluid channels, which are denoted as channels c1 and c2 in FIG. 2. By rotation of the rotor member 25 against the bearing surfaces about a central axis of the valve 21 in accordance with the arrows, the internal fluid channels may be brought into fluidic coupling with various of the ports p1-p6. The internal channel c1 is configured such that up to three consecutive ports of the set of six ports may be brought into fluidic coupling with one another. The other internal channel c2 is configured such that only two adjacent ports may be brought into coupling with each other. The channel c1 may be used to effectively fluidically couple only two adjacent ports if one of its ends is rotated into alignment with one of the plugged ports (p1 or p6).

FIGS. 1E-1G illustrate the operation of the trapping stage and of the elution stages of metabolites and parent compounds within the chromatographic system 1b. FIGS. 1E, 1F and 1G may be compared with FIGS. 1B, 1C and 1D, respectively. Operation of the sampling stage is not illustrated for the chromatographic system 1b since it is essentially identical to the analogous stage within the chromatographic system 1a.

During the trapping stage (FIG. 1E), the multiport valve 21 is configured such that the mixture of sample and mobile phases that flows through fluid tubing line 2f is, after having passed through the first analytical column 18a, mixed with an additional mobile phase (or phases) of a different composition that are provided from fluid tubing line 2g. During this stage, the multiport valve 21 is configured such that separate flows provided from fluid tubing lines 2f and 2g are inputted into opposite ends of the internal channel c1 such that these flows mix internally within the channel c1 and are then output to fluid tubing line 2p. Accordingly, this configuration of the valve 21 replicates the functioning of the selection valve 19 and a tee-junction 8c during analyte trapping within the chromatographic system 1a (FIG. 1B).

During the stage in which metabolite analyte compounds are eluted (FIG. 1F), the multiport valve 21 is configured such that a mobile phase composition provided from fluid tubing line 2g is directed to fluid tubing line 2p and then to the second analytical column 18b. The flow of the appropriate mobile phase, as provided by fluid tubing line 2g and as directed by the valve 21, through the second analytical column 18b causes elution of the metabolite compounds from the column 18b. These eluted metabolite compounds then pass through the valve 133 to the detector 9. This configuration of the valve 21 thus replicates the operation illustrated in FIG. 1C in which the selection valve 19 is in a closed position thus only permitting flow into the gradient valve or tee-junction 8c from the fluid tubing line 2g.

During the stage in which parent analyte compounds are eluted (FIG. 1G), the multiport valve 21 is configured such that the mobile phase carrying the eluted compounds from the first analytical column 18a is directed to fluid tubing line 2k, from which it is carried through valve 133 to the detector 9. Thus, the configuration of the valve 21 during this stage replicates the operation illustrated in FIG. 1D in which the selection valve 19 is configured so as to direct the mobile phase carrying the eluted parent analyte compounds to the fluid tubing line 2k.

FIGS. 3A-3D are diagrams of a third chromatographic system, system 3, in accordance with the present teachings. The system 3 illustrated in FIGS. 3A-3D is similar, in large part to the system 1a shown in FIGS. 1A-1D. However, the system 3 is a simplified version of and differs from the system 1a in that the system 3 lacks the selection valve 19 and the bypass fluid tubing line 2k. As a result, even though the sampling, trapping and metabolite elution stages of the system 3 (FIGS. 3A-3C) operate essentially similarly to the corresponding already-discussed stages of the system 1a (FIGS. 1A-1C), the parent compound elution stage (FIG. 3D) requires that the compounds eluting from the first analytical column 18a pass through the second analytical column 18b on their passage to the detector 9. This step may operate properly provided that the parent analyte compounds are not retained within the second analytical column 18b during this step. The proper operation of this parent elution step (FIG. 3D) therefore requires that the mobile phase composition employed during this step is chosen such that these parent compounds have a strongly preferential affinity for the mobile phase, relative to the stationary phase within the second analytical column 18b.

Figure 4:
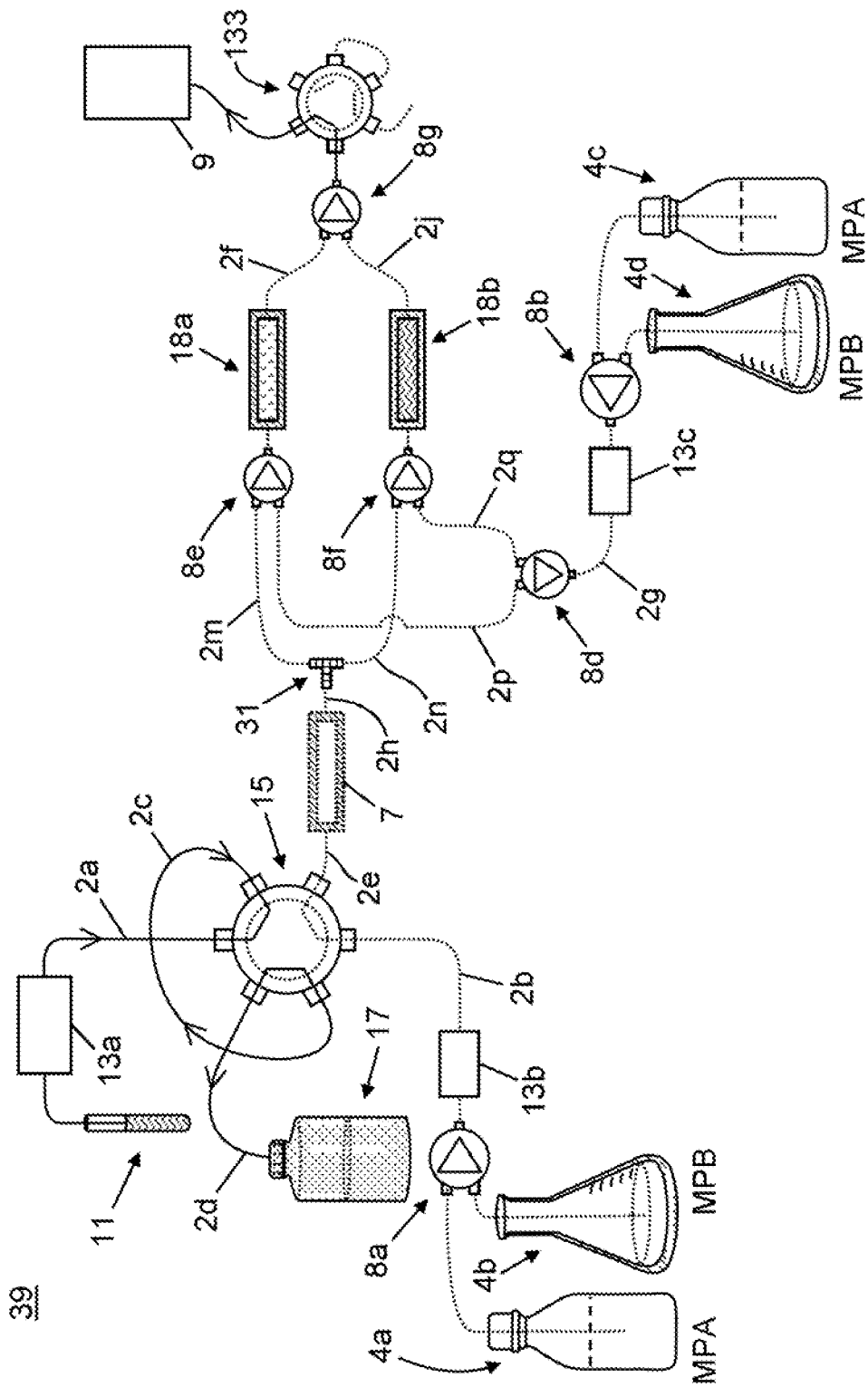
FIG. 4 is a diagram of a fourth chromatographic system in accordance with the present teachings.

FIG. 4 is a diagram of a fourth chromatographic system in accordance with the present teachings. The system 39 illustrated in FIG. 4 comprises many of the same components of the system 1a illustrated in FIG. 1, these similar components being numbered similarly to their numbering in the previously-described FIG. 1. However, in the system 39, the two analytical columns 18a, 18b are configured in a parallel configuration, as opposed to their serial coupling within the system 1a. The fluidic coupling is such that, during the step of trapping analytes on the two analytical columns, fluid flow is divided between the two columns. The fluid flow may be divided between fluid tubing segments 2m and 2n by a common tee-junction 31 as illustrated in FIG. 4 or, alternatively, may be divided by a valve.

During the trapping step, the tee-junction or valve 31 divides the flow of sample and solvents such that a portion of the sample and solvents is delivered to the first analytical column 18a and a second portion is delivered to the second analytical column 18b. In various embodiments, this fluid flow may be divided substantially or approximately equally between the two analytical columns. Likewise, during either trapping or elution steps, the fluid flow of individual solvents MPA and MPB or a mixture of these solvents from solvent sources 4c and 4d may be directed to one or the other of the analytical columns by means of valves 8d, 8e and 8f which are fluidically coupled by fluid tubing segments 2p and 2q. For example, during trapping of analytes on the columns, a mobile phase solvent or solvent mixture delivered from solvent sources 4c and 4d may be mixed, by means of one or the other of the valves 8e and 8f, with the mobile phase solvent mixture delivered from solvent sources 4a and 4b so that the mobile phase composition entering the analytical column 18a is different from the mobile phase composition entering the analytical column 18b. As described previously, such a difference in mobile phase compositions, taken in conjunction with different column properties, will be such that more hydrophilic analytes are retained on one of the columns while the less hydrophilic analytes are retained on the other one of the columns. In the system 39 (FIG. 4), the outflows from the first analytical column 18a and the second analytical column 18b are directed (non-simultaneously) by fluid tubing line 2f and fluid tubing line 2j to valve or tee-junction 8g, after which the two outflows are directed along a common pathway through valve 133 to the detector 9. It is also possible to elute from both columns simultaneously provided that none of the compounds that co-lute in time on the mass spectrometer have similar masses, such as isobars. In this case, the mass spectrometer can be used to separate co-eluting corn pounds that have different molecular weights.

Figure 5A:
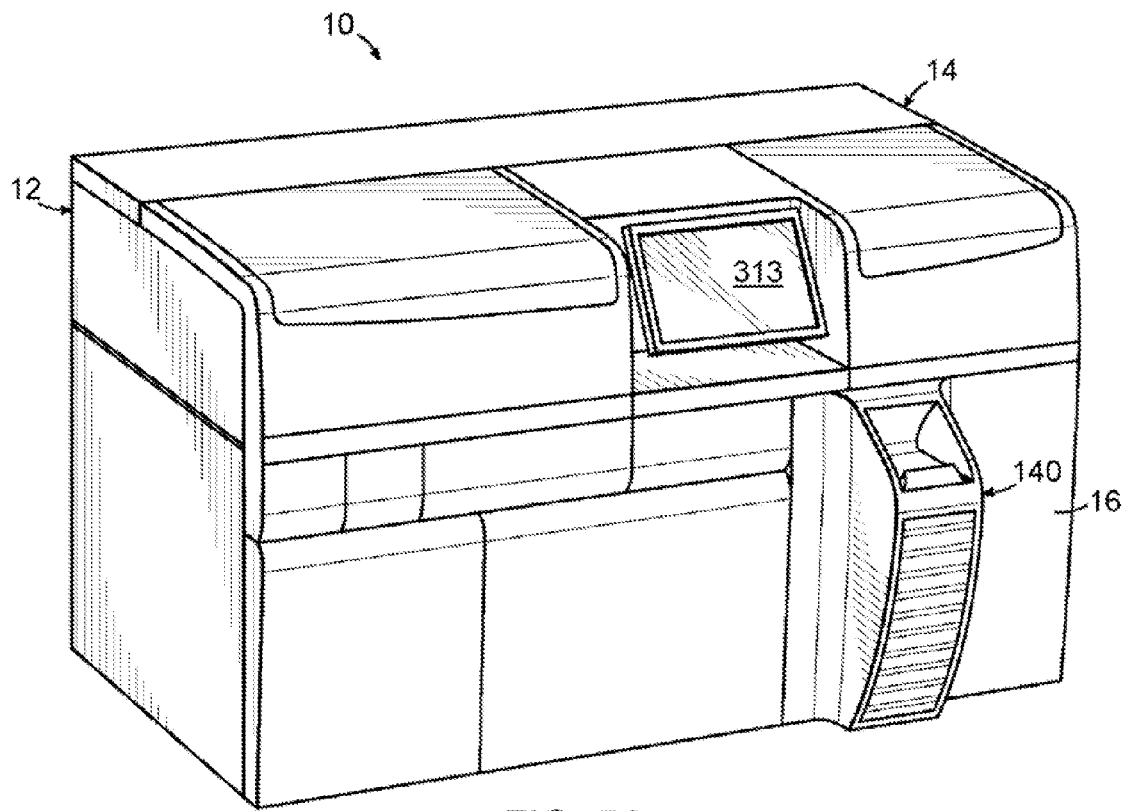
FIG. 5A is a perspective view of an automated sample preparation and analysis system in accordance with some embodiments in accordance with the present teachings.
Figure 5B:
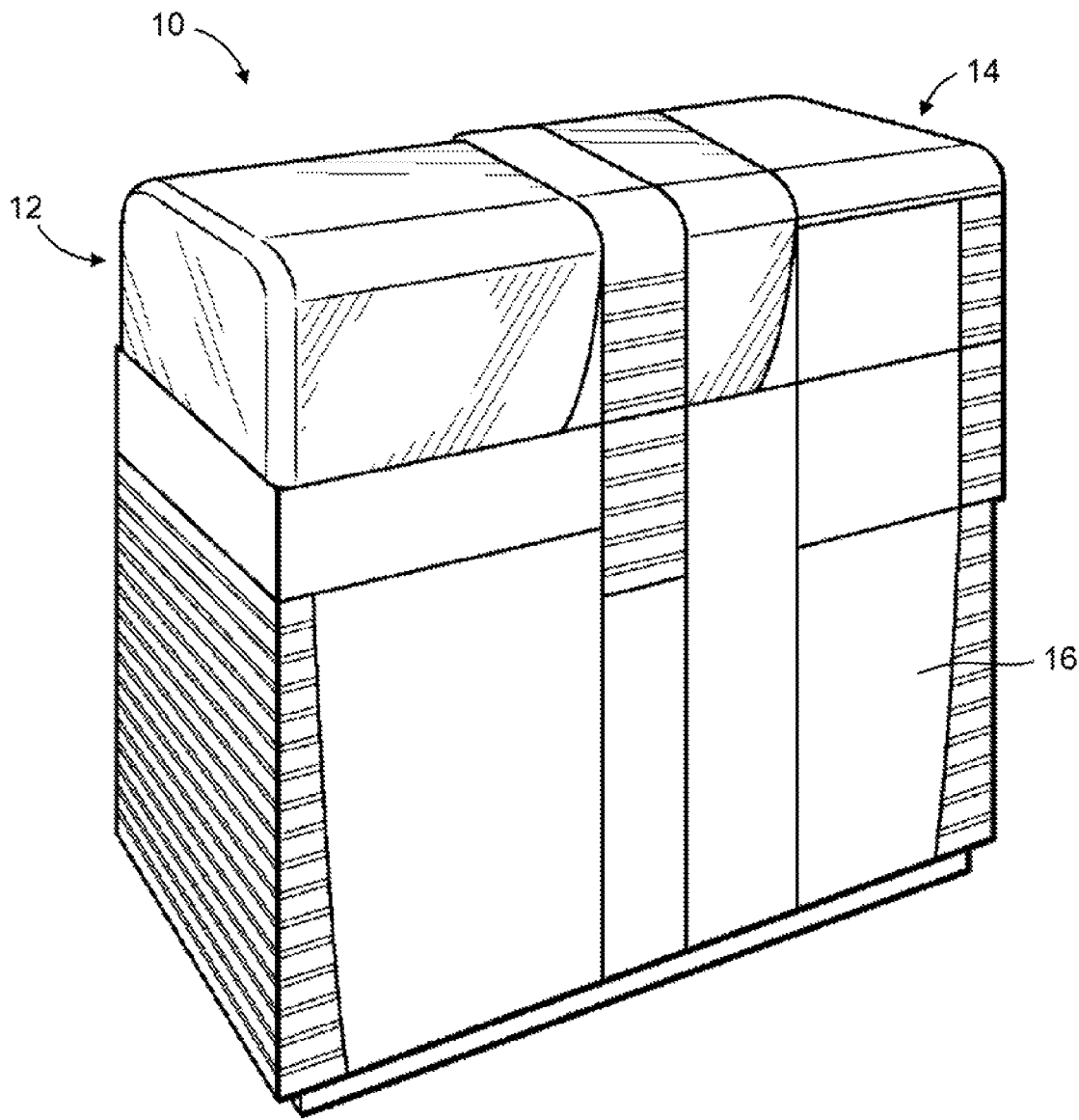
FIG. 5B is a perspective view of another automated sample preparation and analysis system in accordance with various other embodiments in accordance with the present teachings.

The clinical analysis of drug compounds—including pharmaceutical compounds as well as other natural and synthetic drugs of abuse—is now discussed with regard to implementation within an automated sample preparation and analysis system. Such a system has recently been described in the aforementioned international patent application (PCT) publication WO 2012/058632 A1 and various feature of such a system are illustrated in the accompanying FIGS. 5-9. For example, FIG. 5A is a perspective illustration of one exemplary embodiment of an automated sample preparation and analysis system 10 (referred to hereinafter as "system" 10). The system 10 is designed to automatically prepare a sample from a specimen for analysis and to analyze the prepared sample according to a predetermined analyte assay selected from a variety of different or unique analyte assays. As will be described in greater detail below, the exemplary system 10 is particularly designed to perform two distinct laboratory functions, i.e., sample preparation and sample analysis, in combination in an automated system. FIG. 5B, like FIG. 5A, is a perspective illustration of an automated sample preparation and analysis system 10' and where similar numbers with primes refer to similar features.

In one embodiment, the system 10 includes a sample preparation system 12 for preparing various samples and a sample analysis system 14, which includes a suitable analyzer, such as a liquid chromatography mass spectrometer ("LCMS"), for analyzing the prepared samples according to selected analyte assays. The sample preparation system 12 and the sample analysis system 14 are interconnected in an automated manner as will be described in detail below and may, in fact, be enclosed within, a unitary cover 16.

Figure 6:
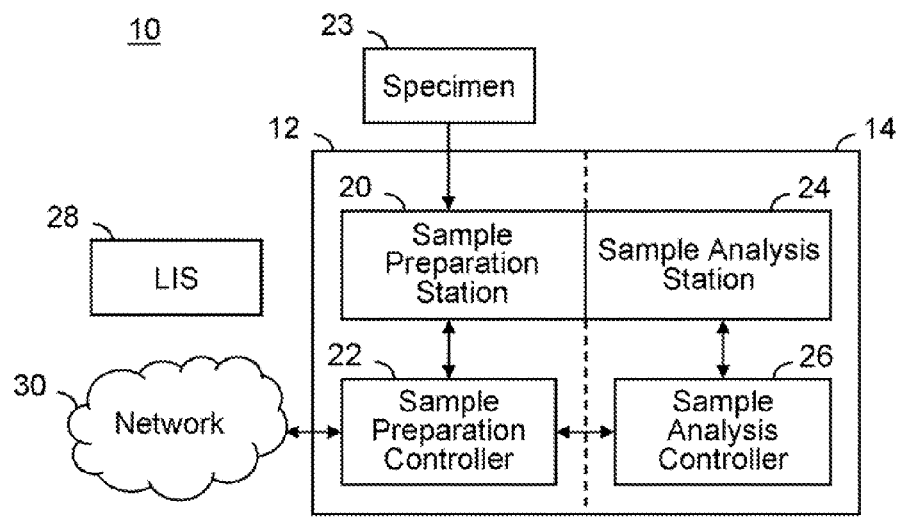
FIG. 6 a general diagrammatic view of the components automated sample preparation and analysis system.

FIG. 6 is a diagrammatic illustration of various components of the system 10. The sample preparation system 12 includes a sample preparation station 20 and a sample preparation controller 22 that controls selected functions or operations of the sample preparation station 20. The sample preparation station 20 is configured to receive one or more specimens 23, to sample the specimens 23 to prepare the samples for analysis according to a variety of preselected analyte assays, and to transport the prepared samples for analysis to the sample analysis system 14. In some embodiments, the sample preparation station 20 is configured to prepare the sample such that the prepared sample is chemically compatible with the sample analysis system 14 according to the selected analyte assay to be, performed by the sample analysis system 14.

Further referring to FIG. 6, in one embodiment the sample analysis system 14 includes a sample analysis station 24 and a sample analysis controller 26 that controls selected functions or operations of the sample analysis station 24. The sample analysis station 24 is configured to receive the prepared sample from the sample preparation station 20 via a transport mechanism described in greater detail below. The sample analysis station 24 then analyzes the prepared sample according to a selected analyte assay to obtain a result for that sample. The sample result is transmitted to the sample preparation controller 22, which may validate the results. If the result is valid, the result may be transmitted to a laboratory information system 28 (illustrated as, and referred to hereinafter, as "LIS" 28) via at least one network 30.

It will be readily appreciated that while FIG. 6 seems to indicate that the sample preparation station 20 and the sample analysis station 24 comprise two opposing sides of the system 10, the systems may encompass the same area or footprint. Indeed, in accordance with the present invention, in some embodiments the sample preparation station 20 and the sample analysis station 24 need not be encompassed within the same housing or unit.

Figure 7A:
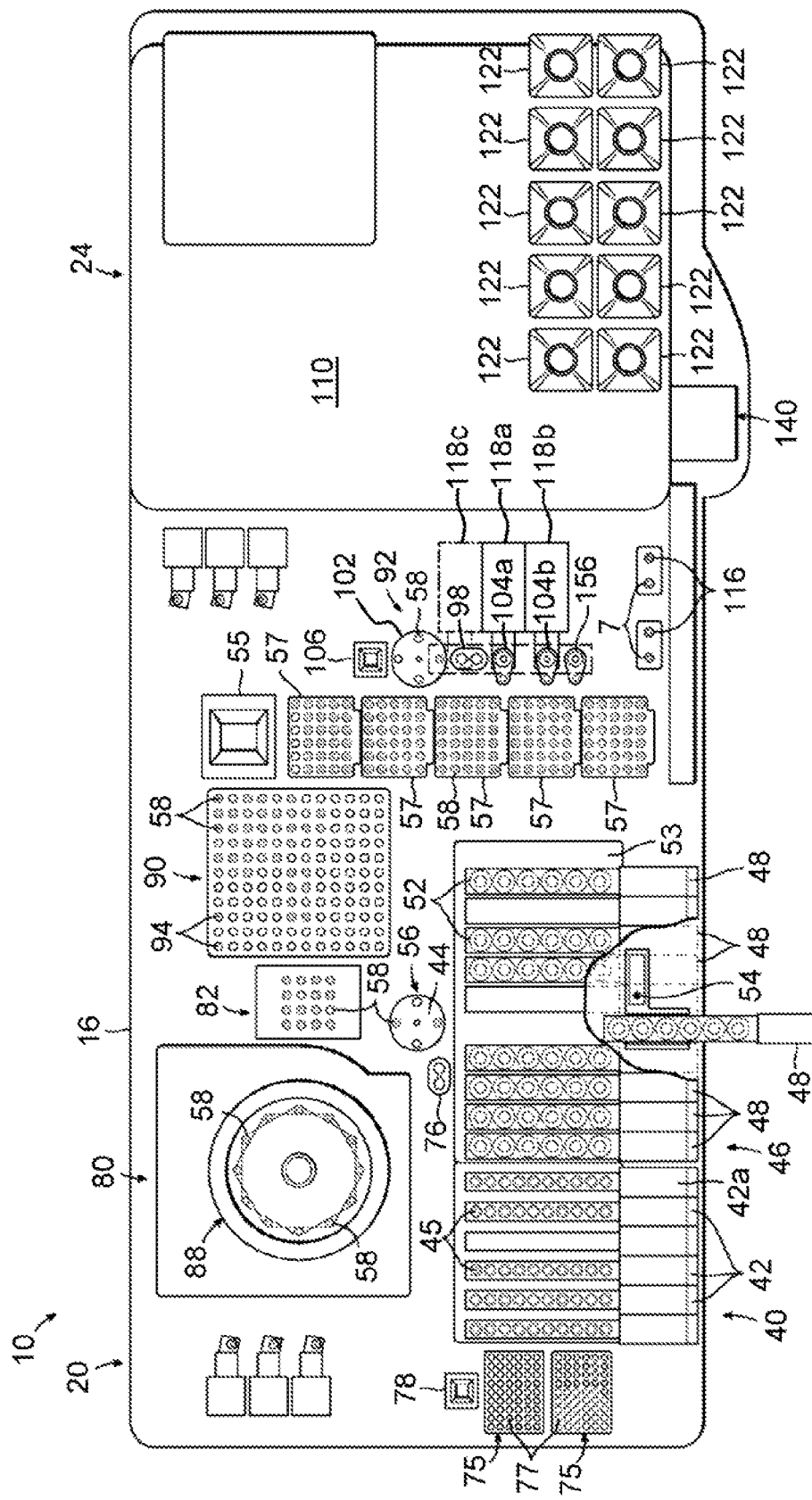
FIG. 7A is a top view of the automated sample preparation and analysis system of FIG. 5A.
Figure 7B:
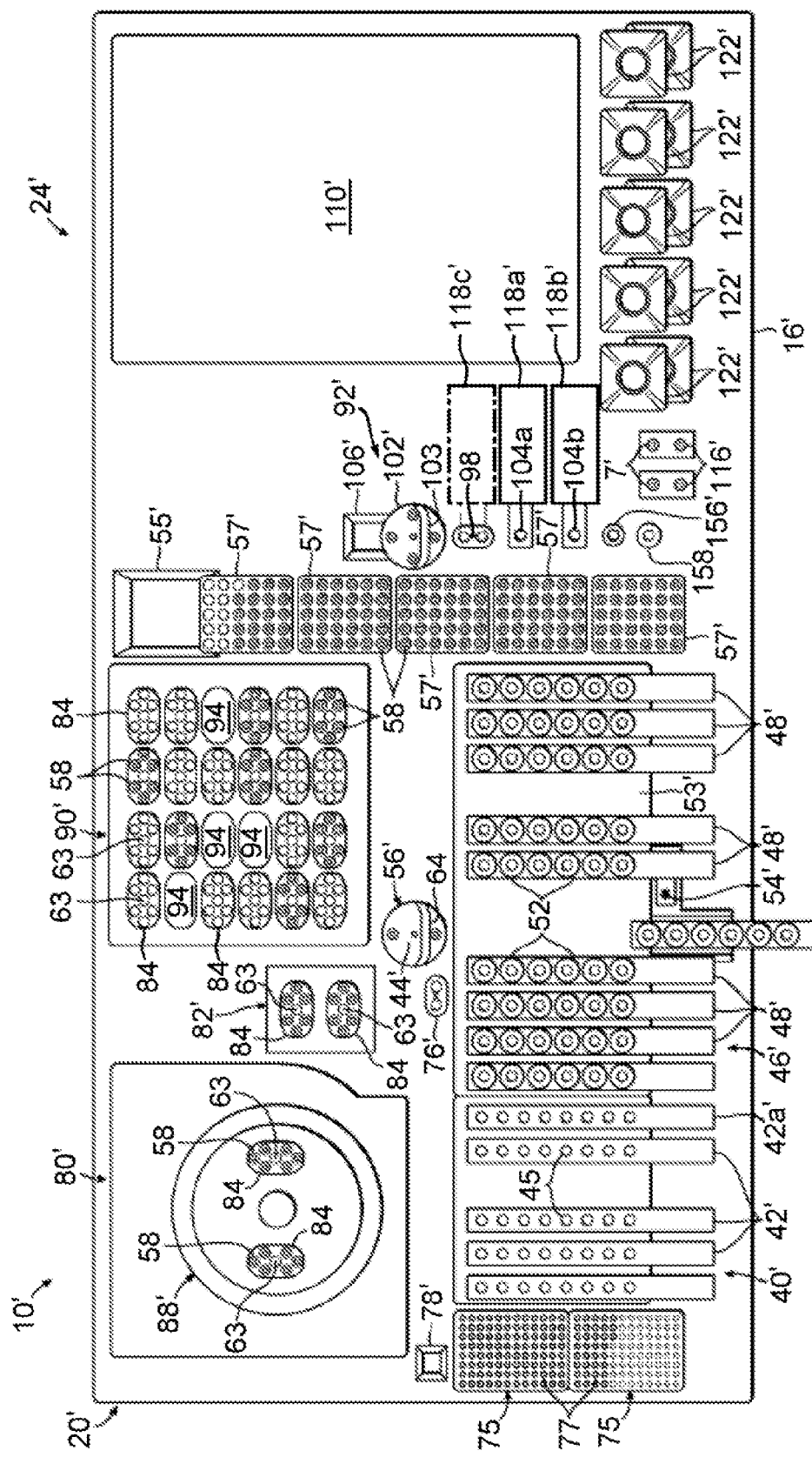
FIG. 7B is a top view of the automated sample preparation and analysis system of FIG. 5B.
Figure 7C:
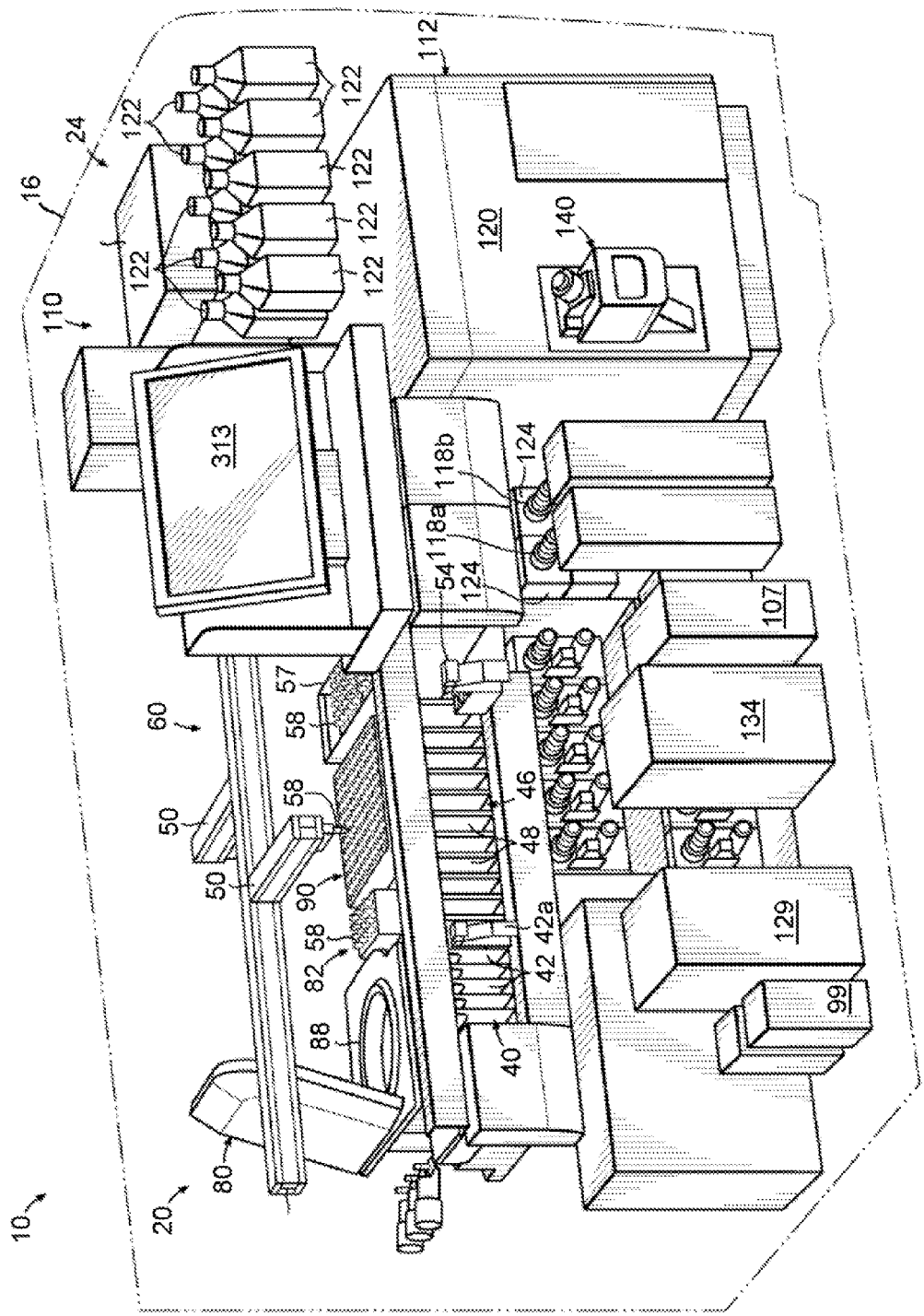
FIG. 7C is a perspective view of the components of the automated sample preparation and analysis system of FIG. 5A.

Turning now to FIGS. 7A-7B, the details of two embodiments of layouts of the sample preparation station 20 and the sample analysis stations 24 associated with the systems 10, 10' of FIGS. 5A and 5B are shown and briefly described below. It would be understood that, for the convenience of discussion, the like reference numerals referring to like features with primes are included herein, though each is not necessary provided explicitly. The sample preparation station 20 includes a specimen dock 40 having one or more specimen racks 42. Each specimen rack 42 includes one or more specimen rack positions capable of holding a specimen container 45 (see, FIG. 7A). The specimen containers 45 are configured to contain the acquired biological or environmental specimens, which may be any specimen containing or suspected of containing an analyte of interest. Patient specimens may include blood, serum, plasma, urine, stool, sputum, brochiallavage, nasopharangeallavage, perspiration, tears, extracts of solid tissue, swabs (from all bodily sites, including skin), cerebrospinal fluid, or saliva, for example Environmental samples may include, for example, food, water, or environmental surface samples. These patient specimens or environmental samples may be analyzed for one or more analytes, which may include, but are not limited to, drugs, pro-drugs, metabolites of drugs, metabolites of normal biochemical activity, peptides, proteins, antibiotics, metabolites of antibiotics, toxins, microorganisms (including bacteria, fungi, and parasites), and infectious agents (including viruses and prions). Further, any of the foregoing samples, alone or in combination, may be suspended in an appropriate media, for example, within a blood culture or a screening booth. The specimen container 45, itself, may include any suitable labware, such as a vessel, a vial, a test tube, a plate, or any other suitable container known in the art. One or more of the specimen racks 42 may be designated, or otherwise labeled (e.g., by placement of the rack 42 within the sample preparation station 20 or with a barcode or an RFID antenna), as priority racks 42a, or STAT, for introducing specimen containers 45 having urgent specimens. Alternatively, urgent specimens may be introduced into a specimen rack 42 and identified as priority or STAT samples by pressing a priority button (not shown) on the instrument or by setting the sample priority using a touch screen display 313 (see FIG. 5A). Urgent specimens may include, for example, emergency department patient specimens or patient specimens containing toxicants or immunosuppressants.

The sample preparation station 20 further includes a reagent station 46 containing multiple reagent racks 48. Each reagent rack 48 includes one or more reagent rack positions capable of holding one or more reagent containers 52 that contain solvents and/or reagents, some of which may be comprised of a volatile liquid. While not necessary, the illustrative embodiment of the specimen racks 42 of the sample dock 40 and the reagent racks 48 of the reagent station 46 have similar construction. In other embodiments, it may be advantageous to include reagent racks 48 having a different structure as compared to the specimen racks 42 such that racks 42 containing biological specimens are not inadvertently inserted into the reagent station 46, In still other embodiments, reagent racks 48 may include distinct labeling, e.g., a barcode or an RFID antenna, as compared with the specimen racks 42. The specimen dock 40 may be configured to accommodate an on-line accession station (not shown) for receiving the specimen vessels 45 from an off-line automated laboratory track system (not shown).

The reagent station 46 may include a cooling station 53 coupled to a thermostat (not shown) and chiller (not shown) to maintain the temperature of the reagent station 46 at a constant, cooled temperature, for example, between about 4° C. and about 10° C. This may aid in reducing the loss of reagent through evaporation and thereby extend the lifetime and activity of the reagents contained therein.

Returning to FIGS. 7A-7B, various reagents may reside within the reagent station 46, including all reagents necessary for the plurality of assay types that are capable of being performed by the system 10. For example, the reagents may include protein precipitation reagents (e.g., acetonitrile, methanol, or perchloric acid), cell lysis reagents (e.g., zinc sulfate, a strong acid), an enzyme digestion with lysozymes, cellulases, proteases, detergents including, without limitation, non-ionic, zwitterionic, anionic, and cationic detergents, protein digestion reagents (e.g., serine proteases such as trypsin, threonine, cysteine, lysine, arginine, or aspartate proteases, metalloproteases, chymotrypsin, glutamic acid proteases, lys-c, glu-c, and chemotrypsin), internal standards (e.g., stabile isotope labeled analytes, heavy isotope labeled peptides, non-native peptides or analytes, structurally similar analogs, chemically similar analogs), antibiotics (for microbiological antibiotic susceptibility testing, or "AST"), protein stabilization agents, including buffers, chaotropic agents, or denaturants, calibration standards, and controls. According to various embodiments, one or more of the reagents may be pre-mixed to form a combined reagent mixture specific for a particular assay or panel of assays.

The reagent station 46 may further include an information acquisition device 54 which, for example, may be a bar code reader or an RFID receiver. The information acquisition device 54, in turn, may receive information associated with a reagent of the particular reagent container 52 or information associated with the particular reagent container 52 itself. A bar code or RFID antenna is imprinted or positioned on a reagent container 52. The bar code or RFID antenna may be configured to provide information associated with the particular reagent or it may contain an identification (such as an identifier) that is cross-referenced with a LookUp Table ("LUT") (not shown) accessible by the sample preparation controller 22 (FIG. 6) (e.g., on the sample preparation controller 22 or on the LIS 28 and accessible by the sample preparation controller 22) and having detailed information regarding the reagent contained therein. The information obtained may be used to identify and/or monitor a respective reagent container 52 and/or the reagent therein. For example, the information may be used to identify the reagent within the reagent container 52, identify the location of the reagent container 52 within the reagent station 46, identify and/or monitor the quantity of reagent remaining in the reagent container 52, and/or identify the expiration date of the reagent within the reagent container 52. Though not specifically shown, the information acquisition device 54 may be mounted onto a track system (not shown) that spans between the specimen dock 40 and the reagent station 46, and by way of one or more motors (e.g., a stepper motor or like device) the information acquisition device 54 may be translated to a position within the specimen dock 40 or the reagent station 46 for receiving a specimen rack 42 or a reagent rack 48. In this way, the information acquisition device 54 may scan the barcode and/or RFID antenna as the specimen containers 45 and/or reagent containers 52 are loaded into the sample preparation station 20. Further, it would be understood that while only one information acquisition device 54 is shown, additional information acquisition devices, in like manner or having an alternate structure, may be included in other portions of the system 10 for tracking samples and the associated tests.

Turning now to an illustrative method of sample preparation, a patient sample (referred to hereinafter as "sample"), or a portion of a particular specimen contained within a specimen container 45 is transferred to an open-top sample vessel 58 (also known as a reaction vessel, but referred to hereinafter as "vessel" 58) to be prepared for analysis. Suitable vessels 58 may include, for example, opentop vessels, vessels having a screw-top cap, vessels having integrated flip-top caps, and vessels having tops with piercable septa. The vessels 58 may be stored (FIGS. 7A-7B) within, and introduced from, a storage station (not shown) of the sample preparation station 20. Within the storage station, the vessels 58 may reside in plates 57 or other appropriate mass storage containers. As various ones of the vessels 58 are transferred and periodically leaving empty plates 57, the plates 57 may be discarded through a waste chute 55 from the sample preparation station 20. When a specimen 23 (FIG. 6) is sampled, one or more vessels 58 are transferred to a sampling station 56 from the storage station by way of a transport assembly 60 (see FIG. 8), The transport assembly 60 may include a robot assembly operating on one or more tracks 50 and configured to move in at least one of an x-y direction, an x-y-z direction, or a rotary direction. While not shown, the transport assembly 60 may further include a gripper, or other like device, to capture and release the vessel 58 or a transport handle 63 (FIG. 7B) associated with a vessel rack 84 (FIG. 7B) to simultaneously transport two or more vessels 58 within the system 10.

In another embodiment, not shown, the transport assembly 60 may include a robot assembly configured to move in at least one of an x-y direction, an x-y-z direction, or a rotary direction and which may include an automated liquid handler, According to this embodiment, the automated liquid handler may aspirate and dispense a volume of a liquid between two or more vessels 58 within the system 10 to transport the liquid between two or more of the stations 20, 24, 40, 46 and the accession station (not shown) within the system 10.

In still other embodiments, the transport assembly 60 may further include carousels, i.e., a circular revolving disc, or autosamplers having, multiple vessel positions therein to provide transport function and allow for a temporary, intermediate vessel storage function. In other embodiments, the transport assembly 60 may further include an information acquisition device (not shown). This information acquisition device may operate in a manner similar to the information acquisition device 54 and be used to identify the vessels 58 as they are moved throughout the sample preparation station 20.

Figure 8:
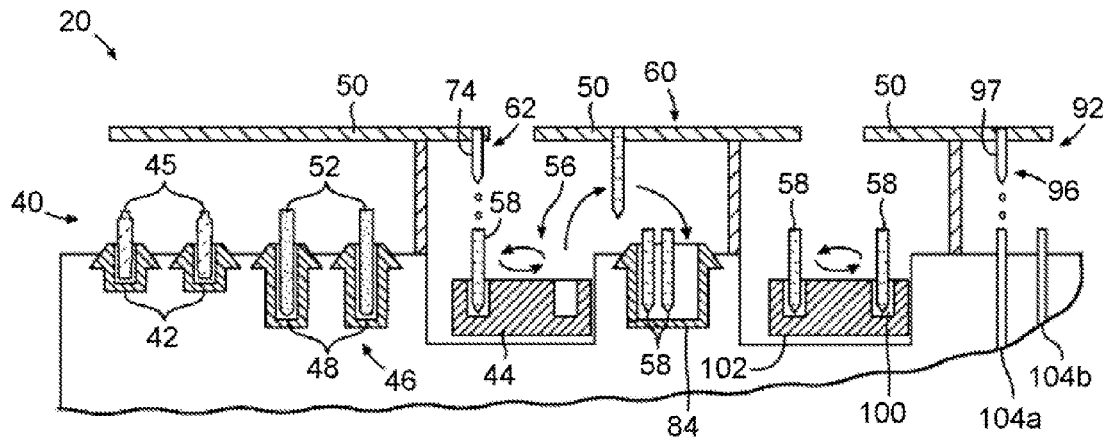
FIG. 8 is a schematic view of a sample preparation station and a transport assembly of the automated sample preparation and analysis system of FIG. 5A.

In the illustrated embodiment, the sampling station 56 includes a rotatable table 44 that rotates each vessel 58 between at least two positions. In one position, the vessel 58 may be received from the transport assembly 60. In another position, the vessel 58 is positioned to receive a portion of the specimen 23 (FIG. 6) via a sample pipette assembly 62 (FIG. 8). The rotatable table 44 may include a vessel cap opening and closing device 64 (FIG. 7B) for opening and closing, a hinged lid (not shown) of the vessel 58 as the vessel 58 is transported between the first and second positions. Accordingly, the hinged lid may be in a closed position when the vessel 58 is delivered to the first position of the sampling station 56. Rotation of the rotatable table 44 moves the vessel 58 to the second position whereby engagement with the opening and closing devices causes the hinged lid to move to an open position.

The sample pipette assembly 62 (FIG. 8) may include a pipette shaft 74 is movable, for example via a robotic device, in one or more of the x-y-z directions and between two or more of the specimen dock 40, the reagent station 46, and the sampling station 56. The pipette shaft 74 may be constructed with a single tip construction that is washed between aspirations at a pipette wash station 76 (FIG. 7A) or, alternatively, may be adapted to receive a disposable tip (not shown) that is then ejected before acquiring a new disposable tip to aspirate a new sample. In the former embodiment, after a sample is dispensed to the vessel 58, the single tip is washed, one or more times, by an appropriate solvent solution, such as by multiple aspirations and dispensing of the solvent in the latter embodiment, the sample preparation station 20 may include a tip storage station 75 (FIGS. 7A-7B) for storage and supplying disposable tips from one or more disposable tip racks 77. After the sample is dispensed to the vessel 58 in this embodiment, the disposable tip is ejected from the pipette shaft into a disposable tip waste chute 78, which is coupled to a larger waste storage container (not shown).

The sample pipette assembly 62 (FIG. 8) may aspirate an aliquot of the specimen 23 (FIG. 6) from the specimen container 45 from within the specimen dock. 40 and dispense the aliquot of the specimen 23 (FIG. 6) into the vessel 58 within the sampling station 56. Additionally, or alternatively, the sample pipette assembly 62 (FIG. 8) may aspirate an aliquot of a desired reagent from one of the reagent containers 52 within the reagent station 46 and dispense the aliquot of the desired reagent into the vessel 58 within the sampling station 56, which may or may not previously include the sample, i.e., the aliquot of the specimen 23 (FIG. 6).

In some embodiments, it may be necessary to mix the specimen 23 (FIG. 6) prior to aspirating. For example, blood specimens may partition over time, i.e., separation of blood cells (erythrocytes, leukocytes, etc.) from the plasma. Some drugs are distributed unequally between the blood cells and the plasma (for example, with 40-50% in erythrocytes, 10-20% in leukocytes, and 30-40% in the plasma). These distributions may be dependent on temperature, hematocrit, and metabolite concentration. Thus, in order to properly measure the particular drug, or other analyte, concentration, a proper sampling of the whole blood must be acquired. One method of mixing the specimen may occur by aspirating and dispensing the specimen 23 (FIG. 6) a number of times (for example, 13 times) with the sample pipette assembly 62 (FIG. 8). The number of aspirations may depend on at least the volume of the specimen container 45, the aspiration volume, and the dispensing "speed." in other embodiments, the pipette shaft 74 (FIG. 8) may shake (move rapidly in at least one dimension) or the sample may be first directed to mixing station (not shown) that is separate from the sampling station 56 to gently mix the specimen 23 prior to sampling.

Following receipt of the aliquot(s) of the specimen 23 (FIG. 6) and/or reagent (which will now be referred to hereinafter for convenience as the "sample") a hinged lid (not shown) of the vessel 58 may be closed via a separate robotic component or the opening and closing device 64. Closing the hinged lid prevents loss of the sample through evaporation. Moreover, because one or more of the liquids dispensed into the vessel 58 may be volatile, sealing of the vessel 58 may be used to prevent evaporation of the one or more volatile liquids and preserve the intended concentration of the sample.

The sample within the vessel 58 is transferred via the transport assembly 60 from the sampling station 56 to a secondary processing station 80 (FIG. 7A). The secondary processing station 80 includes, for example, one or more of a mixing station 82, an incubation station (not shown), and a matrix interference removal station (illustrated as a centrifuge 88) According to one embodiment, each of the mixing station 82 and the matrix interference removal station is capable of accepting either vessels 58 or a vessel rack 84 such that two or more vessels 58 may be processed simultaneously. However, the use of the vessel racks 84 is not required.

The mixing station 82, if included in the secondary processing station 80, may include a shaker, a vortex mixer, or another apparatus capable of accelerating the mixing of the sample within the vessel 58. As shown, the mixing station 82 may be configured to accommodate sixteen vessels 58 (FIG. 7A) or twelve individual vessels 58 via two vessel racks 84 (FIG. 7B).

The incubation station, if included, may also be incorporated in either of an on-line or off-line configuration. The incubation station is configured to heat a sample, with or without additional reagents, at an elevated temperature (by way of example, at a specified temperature ranging from about 27° C. to about 70° C., including, particularly, 37° C., 50° C., or 70° C.) for a predetermined duration of time and based on a selected assay.

The matrix interference removal station, if included within the secondary processing station 80, may be incorporated in either of an on-line or offline configuration (e.g., the on-line configuration being a configuration in which the sample moves between one or more stations or the sample preparation station 20 through fluidic connections without being contained in a vessel 58, the off-line configuration being a configuration in which the sample is transported within a vessel 58 between stations of the sample preparation station 20). In embodiments that include an on-line matrix interference removal station, the analyte-containing prepared sample may flow directly from the matrix interference removal station to the next station, such as through tubing. This second station may include, for example, a second matrix interference removal station (not shown). In embodiments that include an off-line matrix interference removal station, the analyte-containing prepared sample is collected from the matrix interference removal station and placed into a vessel 58 if not already contained in a vessel 58.

The matrix interference removal station is operable to separate one or more of residual proteins, phospholipids, salts, metabolites, carbohydrates, nucleic acids, and/or other substances that may otherwise interfere with subsequent processing or analysis of the desired analytes and prior to transferring the now prepared sample to the sample analysis station 24. In some embodiments, the matrix interference removal station separates contaminants from the analyte-containing prepared sample, or more simply, the "prepared sample" (for example, by separating precipitated solids from a resulting supernatant liquid, wherein the supernatant liquid forms the prepared sample). The matrix interference removal station may include, for example, one or more of a phase separation station (not shown), a centrifuge (illustrated as reference number 88 in FIG. 7A and reference number 88' in FIG. 7B), a sonicator (not shown), a heating station (not shown), a flash freeze station (not shown), an affinity purification station (not shown), or a filtration station not shown). Each embodiment of the matrix interference removal station may be configured to accommodate one or more vessels 58 or one or more vessel racks 84, or the contents of one or more vessels 58, as appropriate.

The matrix interference removal station may include an affinity extraction or purification station, for example, an immunoaffinity extraction or purification system. An exemplary immunoaffinity system may use a Mass Spectrometry Immunoassay ("MSIA") antibody enriched substrate. One suitable, commercially-available MSIA substrate includes those from intrinsic Bioprobes Inc (Tempe, Ariz.) and that are described in U.S. Pat. No. 6,783,672, the disclosure of which is incorporated herein by reference in its entirety. One exemplary MSIA method is described in greater detail in U.S. Pat. No. 6,974,704, the disclosure of which is incorporated herein by reference in its entirety.

After the sample has passed through the secondary processing station 80, the prepared sample is transported via the transport assembly 60 to an analysis staging station 90. The analysis staging station 90 includes two or more vessel positions 94 (FIG. 7A) or two or more vessel rack positions 94' (FIG. 7B) for accepting vessels 58 or vessel racks 84, respectively. In the particular illustrative examples, the analysis staging stations 90, 90' accommodate about one hundred thirty-two vessels 58 (FIG. 7A) or twenty-four vessel racks 84 (FIG. 7B) that are, in turn, capable of accepting up to about six vessels 58 each, for a total of one hundred forty-four vessels 58. Each vessel position 94 may be stationary within the analysis staging station 90 such that once an individual vessel 84 is placed within a vessel position 94 of the analysis staging station 90, its position does not change but for transfer by the transport assembly 60.

While not specifically shown, the analysis staging station 90 may include a cooling system to maintain the temperature of the analysis staging station 90 at a constant controlled temperature, for example, a temperature of about 4° C. to about 10° C. In this way, and along with the hinged lids of the vessels 53 described previously, the rate of degradation or evaporation of the prepared sample is further reduced while the prepared sample is awaiting analysis.

Alternatively, the analysis staging station 90 may include a heating system, or an incubation station, as described above, to maintain the temperature of the analysis staging station 90 at a constant controlled temperature for incubation, for example, a temperature ranging from about 23° C. to about 70° C. Some specimen types, particularly microbiological specimens, may require extended incubation of the otherwise prepared sample prior to analysis.

When a particular prepared sample is selected for analysis, the vessel 58 containing the prepared sample is transferred via the transport assembly 60 from the analysis staging station 90 to an injector station 92, The injector station 92 may include an injector pipette assembly 96 (FIG. 8) to transfer an aliquot of the prepared sample from the vessel 58 to the sample analysis station 24. The injector pipette assembly 96 (FIG. 8) includes a pipette shaft 97 that may be constructed in a manner that is similar to the sample pipette assembly 62 that was described in detail above.

According to the embodiment shown in FIGS. 7A-7B and FIG. 8, a wash station 93 having a solvent supply 99 fluidically coupled thereto is provided to wash the pipette shaft 97 between aspiration-dispensing as necessary. In another embodiment, not particularly shown herein, the pipette shaft 97 may be shaped to receive a disposable tip, which may be provided in addition to or in alternative to the wash station 98.

The injector station 92 may include a rotatable table 102 having a structure that is similar to the sampling station 56 and may include a vessel cap opening and closing device 103 for opening and closing a hinged lid of the vessel 58 as it is transported to a ready position 100 (FIG. 8). Following aspiration of an aliquot of the prepared sample by the injector pipette assembly 96, the vessel 58 may be rotated away from the ready position 100, thereby closing the hinged lid and preparing the vessel 58 for receipt by the transport assembly 69 for transport and release to a storage facility (not shown) or a waste chute 106 leading to the vessel waste storage 107. Disposable pipette tips may also be ejected from the pipette shaft 97 into the waste chute 106.

As described in detail above, a sample of a specimen 23 (FIG. 6) is prepared at the sample preparation station 20 before that prepared sample is moved to the sample analysis station 24, As such, at least some of the movable portions of the sample preparation station 20, including the sampling station 56, the transport assembly 60, the rotatable tables 44, 102, the injector station 92, and the injector pipette assembly 96, acting individually or in concert, may comprise a transport mechanism to transport the prepared sample from the sample preparation system 12 to the sample analysis system 14. One having ordinary skill in the art will appreciate that alternative embodiments of a transport mechanism to transport a prepared sample from a sample preparation system 12 to a sample analysis system 14 may be used without departing from the scope of embodiments of the invention. In the exemplary embodiment, the transport mechanism may comprise the injector pipette assembly 96, which removes an aliquot of the prepared sample for dispensing to the sample analysis station 24.

Turning now to the details of the sample analysis station 24, and in particular to FIGS. 7A-7C and FIGS. 9A-9B, one embodiment of the sample analysis station 24 may be an LCMS system having a liquid chromatography station 110 and a mass spectrometer station 112. The liquid chromatography station 110 (referred to hereinafter as "LC station" 110) may include one, two, or more injection ports 104a, 104b for accepting the aliquot of the prepared sample from the injector pipette assembly 96 for analysis. The injection ports 104a, 104b may be connected on-line to one or more chromatography columns for separation of the prepared sample into analytes of interest eluting at one or more elution times and a plurality of ancillary or waste eluents. As shown in the illustrative embodiments, the LC station 110 includes two separation channels, i.e., LC channels 118a, 118b (a third LC channel 118c shown in phantom).

Figure 9A:
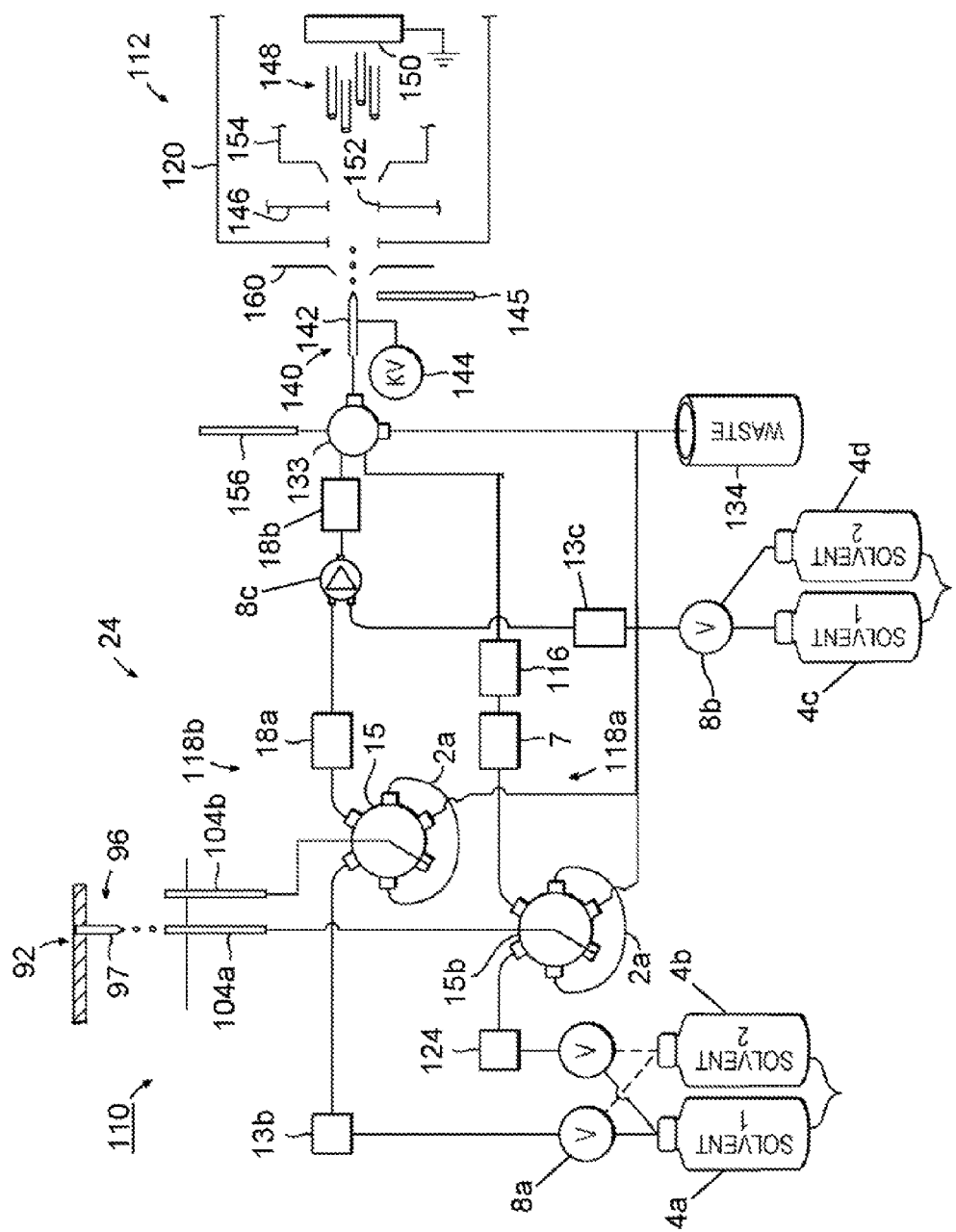
FIG. 9A is a schematic view of a first system comprising a sample preparation station and a sample analysis station of an automated sample preparation, and analysis system in accordance with one embodiment of the present teachings.
Figure 9B:
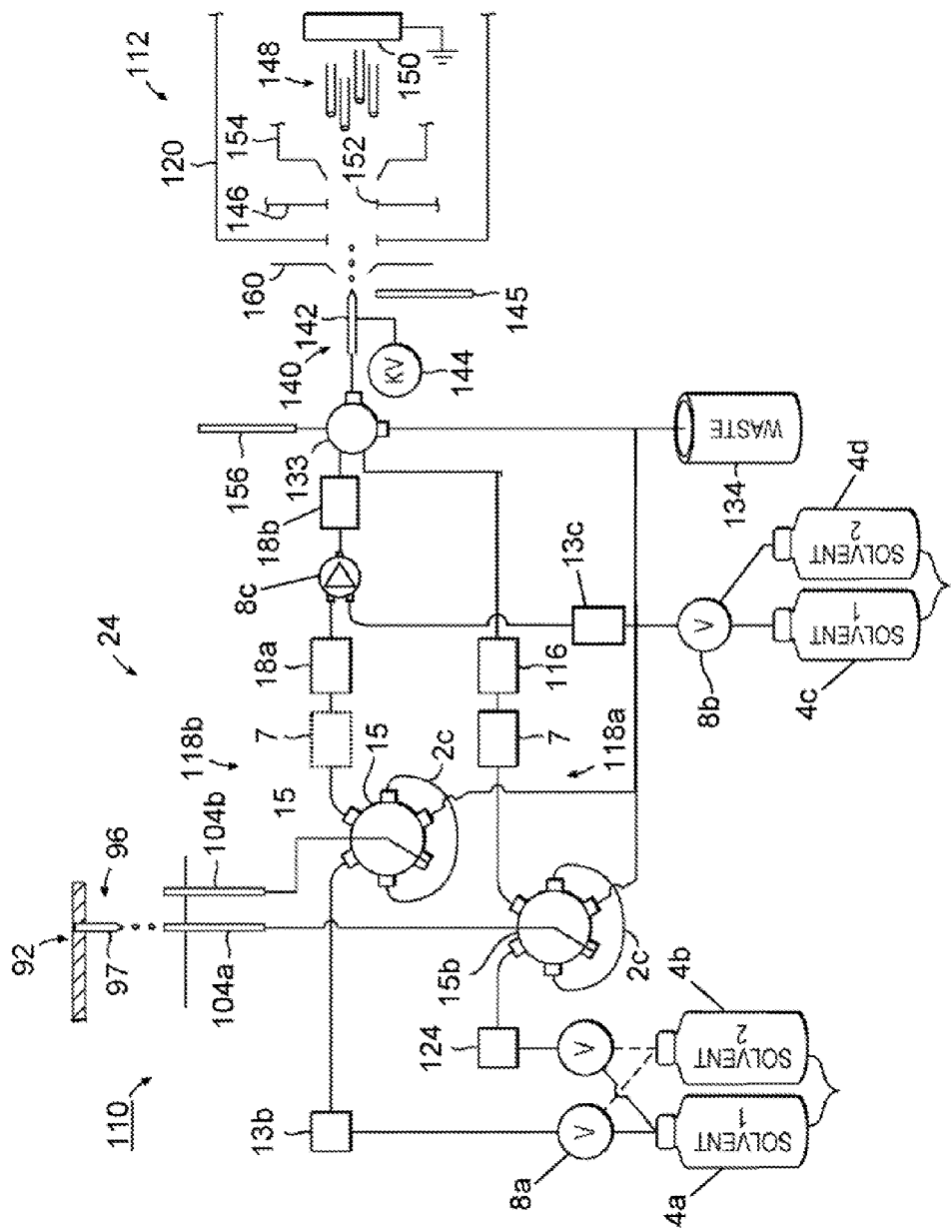
FIG. 9B is a schematic view of a second system comprising a sample preparation station and a sample analysis station of an automated sample preparation and analysis system in accordance with another embodiment of the present teachings.

When the LC station 110 is not configured so as to separate compounds by the hydrolysis-free methods discussed previously in this document, then all LC separation channels may be configured similarly to the LC channel 118a. This channel includes one preparatory column 7 and one analytical column 116, arranged in series. Otherwise, when the LC station 110 is configured so as to separate compounds by hydrolysis-free methods, the LC station may include one channel configured similarly to the LC channel 118b shown in FIG. 9A. As illustrated in FIG. 9A, this channel may include the pair of analytical columns 18a and 18b arranged as previously described in this document. In alternative embodiments, the channel 118b may also include a preparatory column 7 as illustrated in FIG. 9B. In the examples shown in FIGS. 9A and 9B, the channel 118b is configured similarly to the chromatographic system 3 illustrated in FIG. 3. However, this channel could be alternatively configured similarly to the chromatographic system 1a shown in FIGS. 1A-1D, to the system 1b illustrated in FIGS. 1E-1G, to the system 39 illustrated in FIG. 4, or in any alternative fashion in accordance with the present teachings. Each of the two LC channels 118a, 118b is associated upstream with a respective injector port 104a, 104b and associated downstream with a single mass spectrometer 120 of the mass spectrometer station 112 in a manner that enables multiplexing or staggered sample introduction into the mass spectrometer 120 as described in detail below.

The preparatory column 7, according to some embodiments, may be a size exclusion affinity liquid chromatography column used for, in essence, matrix interference removal. The analytical column 116 included in the LC channel 118a may be a reversed-phase LC column for analyte isolation. Exemplary embodiments include a Cyclone P 0.5×50 mm TURBOFLOW size exclusion affinity liquid chromatography column (Thermo Fisher Scientific, Inc., Waltham, Mass.), described in detail in U.S. Pat. Nos. 5,772,874; 5,919,368; and 6,149,816, the disclosures of which are all of which are hereby incorporated herein by reference in their entireties, and a Hypersil GOLD PEP 2.1×50 mm, 1.9 μm UHPLC analytical column (Thermo Fisher Scientific, Inc., Waltham, Mass.). The columns, according to additional embodiments, may be capillary columns (having an internal diameter of approximately 300 μm), nano columns (having an internal diameter ranging from about 74 μm to about 100 μm), available in packed tip formats, standard packed formats, and biphasic columns for two-dimensional work, for example. In other embodiments, the preparatory column 7 may be a conventional size exclusion column or any other liquid chromatography column that may be utilized as a matrix interference removal device.

The selection of the appropriate preparatory and analytical columns 7, 116 of the LC channel 118a may be based, at least in part, on the ability of this LC channel to provide a range of retention times for analytes of interest versus the eluent. Conventionally, the preparatory and analytical columns 7, 116 are matched for a particular analyte from a particular type of sample; however, the matching of columns 7, 116 may vary from one assay type to another.

Figure 11:
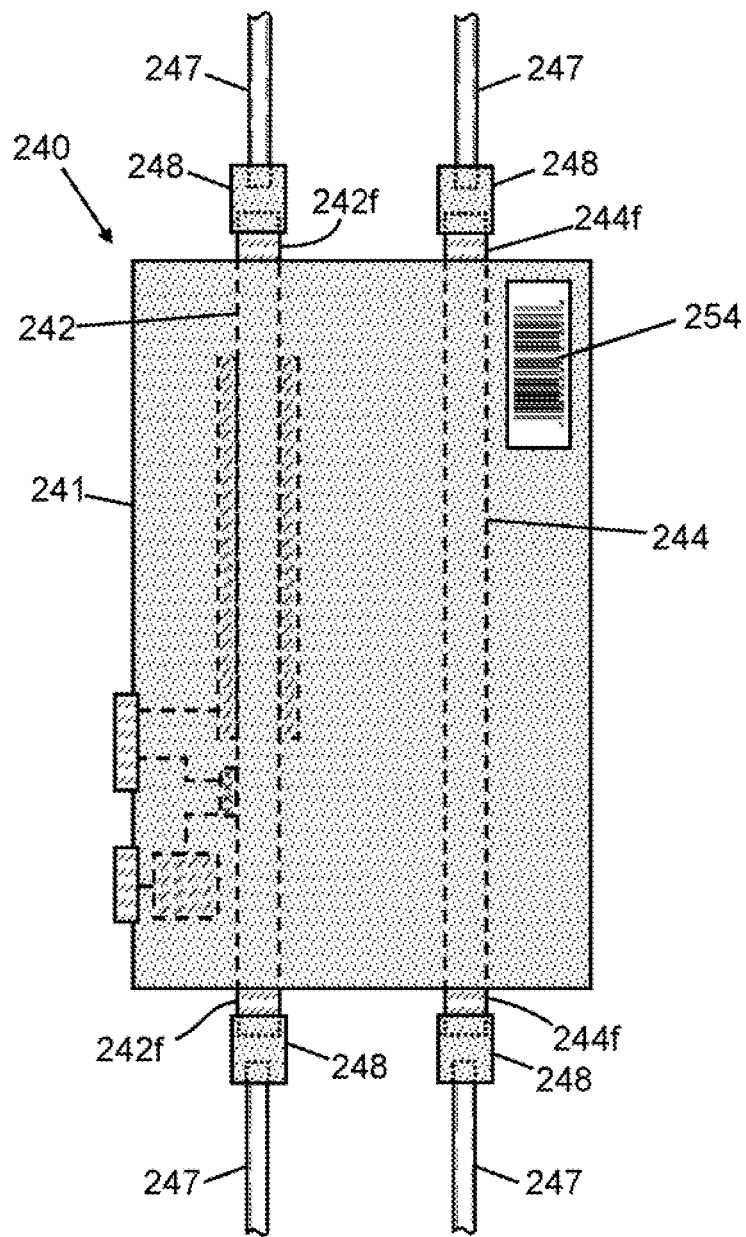
FIG. 11 is a schematic diagram of a modular cartridge configuration which may be used for insertion and removal of pairs of analytical columns matched in accordance with the present teachings.

The LC channel 118b may be readily converted back and forth between its configuration as shown in FIG. 9A and an alternative configuration that is similar or identical to the configuration of the channel 118a. Such conversions may be facilitated by providing the pair of columns 7, 116 and the pair of columns 118a, 118b within modular interchangeable cartridges, each cartridge comprising two columns that are mated or matched so as to operate in conjunction with one another. For example, FIG. 11 schematically illustrates a dual-column chromatography cartridge which may be used for this purpose. Additional details of the apparatus shown in FIG. 11 are described in co-pending international PCT Appl. No. PCT/US2011/058229 which is published as international application publication No. WO 2012/058515 A2 and is assigned to the assignee of this invention and which is hereby incorporated by reference herein in its entirety. The dual-column chromatography cartridge 240 shown in FIG. 11 comprises a housing 241 having two chromatography columns—a first column generally indicated as column 242 and a second column generally indicated as column 244—at least partially contained therein. Preferably, but not necessarily, the columns 242, 244 are affixed to the housing 241. The two columns in each cartridge may be matched for purposes of conducting chromatographic separations of a specific analyte (or analytes), For instance, in a first cartridge, the first column 242 may comprise the cleanup or preparatory column while 7 the second column 244 of the same cartridge comprises the single analytical column 116. In a second cartridge that is interchangeable with the first cartridge, the first column 242 may comprise the first analytical column while 18a the second column 244 comprises the second analytical column 18b.

The first column 242 comprises two column end fittings 242f with one such end fitting at each of the two column ends. Likewise, the second column comprises an end fitting 244f at each of its two ends. As is known, column end fittings are attachment points for fluidic connections to external tubing. Accordingly, connectors 248 are employed in order to connect the two end fittings of the first column 242 to a fluid tubing lines as well as to connect the two end fittings of the second column 244 to other fluid tubing lines. Such fluid tubing lines are shown generally as fluid lines 247 in FIG. 11 but may comprise various fluid tubing, lines as shown in FIG. 1, FIG. 3, FIG. 4 or FIGS. 9A-9B (such fluid tubing lines unlabeled in FIGS. 9A-9B). The cartridge 240 may include a passive identification feature (an indicator or identifier), e.g., a barcode 254 or an RFID module, etc. that may be employed to identify the cartridge and its associated chromatography methods to external apparatus/software. For instance, either of the automated sample preparation and analysis systems 10, 10' may include a barcode reader (not shown) or other apparatus capable of interpreting the passive identification feature, the reader or other apparatus being electronically connected to the sample preparation controller 22 (FIG. 6). This feature may enable system software to be able to automatically verify that the columns within an inserted cartridge are appropriate for an analysis protocol currently being conducted by the system.

Turning again to FIGS. 7A, 7B, 9A and 9B, the sample analysis station 24 includes a separate injection port 156 that is associated with the valve 133 and therefore by-passes the LC channels 118a, 118b. The injection port 156 may be used for injecting a calibration standard or a control standard for performing a calibration or control analysis respectively as appropriate. In some embodiments, a calibration solution supply 158 (FIG. 7B) may be provided near the injection port 156 for ease of access when a calibration standard is necessary. For clarity of discussion of the mass spectrometer 120 hereafter, only the prepared sample injections will be discussed. Yet it will be understood that a sample calibration standard or control standard injected via the injection port 156 would be analyzed in a similar manner.

The injected, prepared sample moves through the columns 7, 116 of the LC channel 118a in a known manner or through the columns 7, 18a and 18b of the LC channel 118b in the manner described previously in this document. The movement of the sample and any solvents along the channel 118a is such that at least one of the analytes of interest will elute off the columns 7, 116 at a retention time that differs from the retention time of other analytes of interest and/or the matrix components, i.e., eluents. The eluents and analytes from both of the first and second LC channels 118a, 118b are directed into the valve 133 where the eluents are directed into the waste container 134 while the analytes are directed to an ionization source 140 of the mass spectrometer station 112. Alternative methods of sample introduction for some samples may include, but are not limited to, on-line methods (such as, flow injection analysis, direct infusion, and injection loops) and off-line methods (such as, solid phase extraction, blood spot surface coatings, matrix-assisted laser desorption/ionization ("MALDI") plate coatings, or coatings on general surfaces), may also be used to introduce the sample to the mass spectrometer 120.

As shown in FIGS. 9A-9B, an atmospheric pressure ionization (either electrospray ionization ("ESI") or atmospheric pressure chemical ionization ("APCI") device (referred to generally herein as "nebulizing ionizer") is used for ionizing the analytes received by the ionization source 140. In that regard, the nebulizing ionizer includes a capillary, probe, or needle (referred hereinafter as "needle" 142) having a solvent conduit therein (not shown) and surrounded by a gas conduit therein (not shown). An outlet of the gas conduit is positioned about 0.1 mm to about 0.2 mm proximally to an outlet of the solvent conduit. In ESI operation a voltage generator 144 is electrically coupled to the needle 142 and is operable to create a high voltage difference between the needle 142 and the counter-electrode that is may be at the mass spectrometer 120.

In use, a solvent is supplied to the solvent conduit at a rate ranging from about 400 µL/min to about 2000 µL/min; however, one of ordinary skill in the art will readily appreciate that the solvent supply varies with the particular ionization source 140 selected. The particular solvent used is dependent on the chemical nature of the analyte in study, and the methodology for selection of an appropriate solvent is well known to those of ordinary skill in the art. A gas, typically an inert gas, such as N2, is supplied to the gas conduit at pressures ranging from about 0 bar to about 7 bar. The voltage generator 144 is activated and provides a voltage potential, typically ranging from about −5 kV to about 5 kV, to the solvent within the needle 142.

In APCI operation, the voltage generator 144 is electrically-coupled to a corona discharge electrode 145 positioned distal to the outlets. The high voltage applied to the corona discharge electrode 145, if present, is operable to ignite a plasma which aids in the ionization of the nebulized solvent, however other ionization methods may be used and are generally known in the art. The plasma causes the ionization of the solvent and analytes(s), and a portion of the charged solvent/analyte(s) will enter into the mass spectrometer 120 as gas phase ions of the analytes ("gas phase ions"). A ion source that is switchable between ESI and APCI modes is described in co-pending U.S. application Ser. No. 13/280, 069, titled "Combined Ion Source for Electrospray and Atmospheric Pressure Chemical Ionization" filed on Oct. 24, 2011, the disclosure of which is incorporated herein by reference in its entirety.

A skimmer 160, positioned distal to the corona discharge electrode 145, acts in conjunction with an auxiliary gas (not shown, but directed between the outlets and the skimmer 160) to contain and/or focus the gas phase ions into a vacuum chamber of the mass spectrometer 120. The auxiliary gas may be supplied at rates that range generally from about 0 L/min to about 15 L/min.

Referring still to FIGS. 9A-9B, the illustrative example of the mass spectrometer 120 includes an interface 146 with the ionization source 140, a mass filter 148, and an ion detector 150, The regions containing the mass filter 148 and the ion detector 150 are maintained under vacuum. This interface 146 includes an orifice 152 that provides an opening into a higher vacuum chamber containing the mass filter 148 while maintaining vacuum pressures.

In the illustrated example, the mass filter 148 is shown to be a conventional quadrupole; however, those skilled in the art will understand the determination by which the appropriate mass filter modality for a given assay is selected. In fact, other mass spectrometer embodiments may include, for example, a single quadrupole modalities, time-of-flight ("TOF"), Fourier Transform (FT), electrostatic trap or ion trap ("OT") modalities, or hybrid modalities, such as Q-TOF, TOF-TOF, Q-Exactive, LTQ-Oorbitrap, and LTQ-FT, or a mass spectrometer modified for proton transfer.

EXAMPLES

Figure 12:
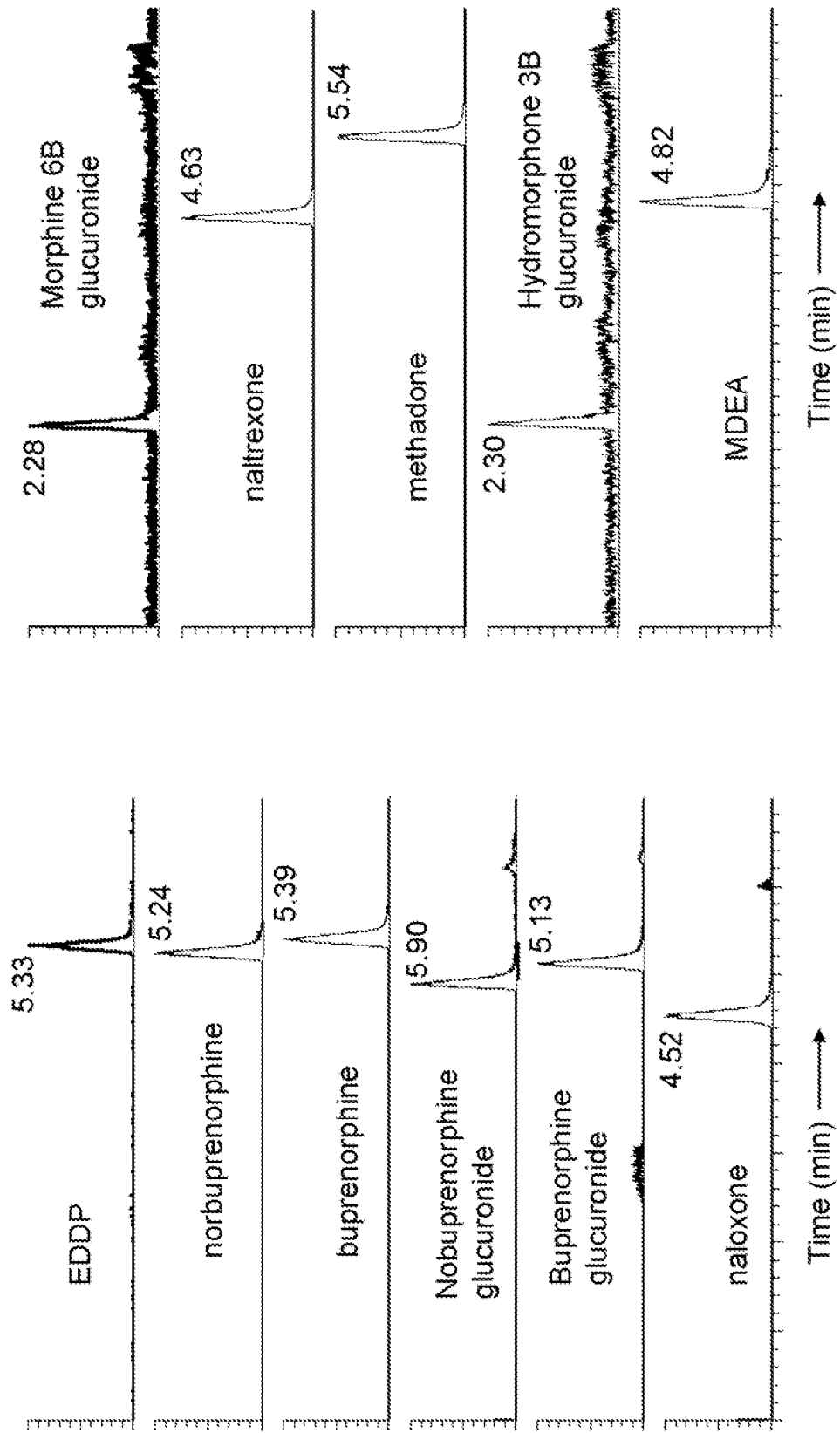
FIG. 12 is a set of chromatograms of various analytes in urine samples, as observed using the system illustrated in FIG. 1.

FIG. 12 shows a set of chromatograms of various drug compounds and drug metabolites obtained using an experimental configuration similar to those illustrated in FIG. 1 and a mass spectrometer detector. Each chromatogram represents detection of the molecular ion of each compound provided in a respective urine sample. To obtain these results, an Accucore™ C18 column was used as the first analytical column 18a in the series and a Synergi™ Polar RP column was used as the second column 18b, as noted previously in this document. According to the experimental configuration and method (FIG. 1), the first-eluting analytes are those from the second column in line, followed by the analytes from the first column. Thus, as shown in FIG. 12, the relatively-more-hydrophilic compounds retained on the second column exhibit retention times generally less than four minutes and the relatively-less-hydrophilic compounds retained on the first column exhibit retention times greater than four minutes. As illustrated in FIG. 12, the various compounds are successfully separated between columns based on their hydrophobicity and compounds retained on any one column may be successfully separated and quantified based on their respective retention times. These include the parent compound methodone and its Phase-I metabolite EDDP and the parent compound buprenorphine as well as its Phase-I metabolite norbuprenorphine and its Phase-II metabolites buprenorphine glucoronide and norbuprenorphine glucoronide, all of which are successfully separated from one another on the first column.

CONCLUSIONS

This teachings disclosed herein provide solutions to two problems. Firstly, by measuring both the metabolites and parent compounds without performing hydrolysis of the metabolites, the methods and apparatus taught herein save time, money and resources compared to conventional methodology. The disclosed methods remove the variability seen when using enzymes to do the hydrolysis because additional calculations of activity are no longer necessary, thereby making the methods less complicated and easier to perform. These methods also reduce degradation caused by using strong acids or bases to perform hydrolysis. These methods further reduce degradation by removing, the need to heat the samples over long periods of time (usually over night) at high temperatures. Secondly, the method disclosed herein overcome issues with the challenging chromatography associated with the secondary metabolites and their parents to measure all the components in a single run.

The discussion included in this application is intended to serve as a basic description. The various drawings and associated descriptions are provided by example only and are not intended to be limiting of the invention. Thus, although the present invention has been described in accordance with the various embodiments shown and described, one of ordinary skill in the art will readily recognize that there could be variations to the embodiments and those variations would be within the scope of the present invention as claimed. The reader should be aware that the specific discussion may not explicitly describe all embodiments possible; many alternatives are implicit. For example, one of ordinary skill in the art may readily envision that many practical implementations of the invention may employ additional valves, solvent sources, fluid tubing lines and, possibly, chromatographic columns. Such additional components may be provided, for example, in order to flush fluids from the system between analytical runs, to enable cleaning or buffer solutions to be passed through the various fluidic components or to enable selection between pathways that are set up to operate according to alternative chromatographic analysis methods. One of ordinary skill in the art may also envisage different implementations of valves (for example, valves having different numbers of ports) or fluidic connections (for example, fluidic lines connected to a valve in a different order) than those shown herein. Accordingly, many modifications may be made by one of ordinary skill in the art without departing from the scope and essence of the invention as claimed. Neither the description nor the terminology is intended to limit, the scope of the invention. All patent application disclosures, patent application publications or other publications mentioned herein are hereby explicitly incorporated by reference herein as if fully set forth herein.

What is claimed is:

1. An automated sample preparation and analysis system comprising:
    (a) an automated sample preparation station for preparing a plurality of samples in accordance with a plurality of assays;
    (b) a sample analysis station for automatically performing the plurality of assays; and
    (c) a transport mechanism for transporting prepared samples from the sample preparation station to the sample analysis station,
    wherein the sample analysis station comprises:
        (i) a first supply of chromatographic mobile phase;
        (ii) a second supply of chromatographic mobile phase;
        (iii) a first chromatographic column comprising an outlet end and an inlet end that is configured to receive a chromatographic mobile phase from the first supply and a portion of a prepared sample;
        (iv) a second chromatographic column comprising an inlet end and an outlet end;
        (v) at least one valve or tee-junction having a first outlet port fluidically coupled to the second chromatographic column inlet end, a second outlet port, a first inlet port fluidically coupled to the first chromatographic column outlet end and a second inlet port fluidically coupled to the second supply of chromatographic mobile phase;
        (vi) a mass spectrometer; and
        (vii) a multi-port valve comprising a first inlet port of the multi-port valve fluidically coupled to the second outlet port of the valve or tee-junction, a second inlet port of the multi-port valve fluidically coupled to the second chromatographic column outlet end, and an outlet port of the multi-port valve fluidically coupled to the mass spectrometer;
        wherein the at least one valve or tee-junction and the multi-port valve are mutually configurable such that:
            in a trapping configuration, the second chromatographic column inlet end is fluidically coupled to both the first chromatographic column outlet end and the second supply of chromatographic mobile phase and the second chromatographic column outlet end is fluidically coupled to a waste line;
            in a first elution configuration, the second chromatographic column inlet end is fluidically coupled to the second supply of chromatographic mobile phase and the second chromatographic column outlet end is fluidically coupled to the mass spectrometer; and
            in a second elution configuration, the first chromatographic column outlet end is fluidically coupled to the mass spectrometer and the second chromatographic column outlet end is fluidically coupled to the waste line.

2. An automated sample preparation and analysis system as recited in claim 1, wherein the first and second chromatographic columns comprise different respective stationary phases.

3. An automated sample preparation and analysis system as recited in claim 1, wherein one of the two chromatographic columns performs analyte separation by hydrophilic interaction (HILIC) chromatography and the other of the two columns performs analyte separation by reversed-phase chromatography.

4. An automated sample preparation and analysis system as recited in claim 1, wherein the at least one valve or tee-junction comprises:
    a selection valve comprising:
        the first inlet port of the at least one valve or tee-junction;
        the second outlet port of the at least one valve or tee-junction; and
        a selection valve outlet port; and
    a gradient valve or tee-junction comprising:
        the second inlet port of the at least one valve or tee-junction;
        the first outlet port of the at least one valve or tee-junction; and
        a third inlet port of the at least one valve or tee-junction fluidically coupled to the selection valve outlet port.

5. An automated sample preparation and analysis system as recited in claim 1, wherein the at least one valve or tee-junction comprises a second multi-port valve comprising:
    the first outlet port of the at least one valve or tee-junction;
    the first inlet port of the at least one valve or tee-junction;
    the second outlet port of the at least one valve or tee-junction; and
    the second inlet port of the at least one valve or tee-junction,
    wherein the second multi-port valve is configured to mix fluids received at the first and second inlet ports of the at least one valve or tee-junction and to deliver the mixture to the second outlet port of the at least one valve or tee-junction.

6. An automated sample preparation and analysis system as recited in claim 1, wherein each of the first and second supplies of chromatographic mobile phase comprises:
    a source of a first chromatographic mobile phase solvent;
    a source of a second chromatographic mobile phase solvent;
    a gradient valve fluidically coupled to the source of the first chromatographic mobile phase solvent and to the source of the second chromatographic mobile phase solvent; and
    a fluidic pump fluidically coupled to the gradient valve.

7. An automated sample preparation and analysis system comprising:

(a) an automated sample preparation station for preparing a plurality of samples in accordance with a plurality of assays;
(b) a sample analysis station for automatically performing the plurality of assays; and
(c) a transport mechanism for transporting prepared samples from the sample preparation station to the sample analysis station, wherein the sample analysis station comprises:
   (i) a first supply of chromatographic mobile phase;
   (ii) a second supply of chromatographic mobile phase;
   (iii) a tee-junction or first valve that is configured to receive a first fluid comprising a chromatographic mobile phase from the first supply and a portion of a prepared sample and to divide the first fluid into a first portion and a second portion;
   (iv) a second valve configured to receive a second fluid comprising a chromatographic mobile phase from the second supply and to divide the second fluid into a first portion and a second portion;
   (v) a first chromatographic column comprising an outlet end and an inlet end configured to receive the first portion of the first fluid and the first portion of the second fluid;
   (vi) a second chromatographic column comprising an outlet end and an inlet end configured to receive the second portion of the first fluid and the second portion of the second fluid;
   (vii) a mass spectrometer; and
   (viii) a third valve coupled between the mass spectrometer and both of the outlet end of the first chromatographic column and the outlet end of the second chromatographic column.

8. An automated sample preparation and analysis system as recited in claim 7, wherein the first and second chromatographic columns comprise different respective stationary phases.

9. An automated sample preparation and analysis system as recited in claim 7, wherein the third valve is operable to direct, to the mass spectrometer, either exclusively an outflow from the outlet end of the first chromatographic column or exclusively an outflow from the outlet end of the second chromatographic column.

10. An automated sample preparation and analysis system as recited in claim 1, wherein the second chromatographic column comprises a unique inlet end and a unique outlet end.

* * * * *